(12) United States Patent
Christensen et al.

(10) Patent No.: US 7,244,879 B2
(45) Date of Patent: Jul. 17, 2007

(54) NUCLEOTIDE SEQUENCES AND POLYPEPTIDES ENCODED THEREBY USEFUL FOR MODIFYING PLANT CHARACTERISTICS IN RESPONSE TO COLD

(75) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/248,547

(22) Filed: Oct. 12, 2005

(65) Prior Publication Data

US 2007/0083953 A1    Apr. 12, 2007

(51) Int. Cl.
*A01H 1/00*    (2006.01)
*C07H 21/04*   (2006.01)
*C12N 5/14*    (2006.01)
*C12N 15/09*   (2006.01)

(52) U.S. Cl. .................. 800/298; 435/468; 435/419; 435/320.1; 800/289; 536/23.1

(58) Field of Classification Search .......... None
See application file for complete search history.

(56) References Cited

U.S. PATENT DOCUMENTS

2004/0031072 A1* 2/2004 La Rosa et al. ............ 800/278

FOREIGN PATENT DOCUMENTS

WO    WO2005/098015    10/2005

OTHER PUBLICATIONS

Guo et al. (PNAS, 101: 9205-9210, 2004).*
See Keskin et al. (Protein Science, 13:1043-1055, 2004).*
Thornton et al. (Nature structural Biology, structural genomics supplement, Nov. 2000). 991-994.*

* cited by examiner

*Primary Examiner*—Phuong Bui
*Assistant Examiner*—Vinod Kumar
(74) *Attorney, Agent, or Firm*—Birch, Stewart, Kolasch, Birch, LLP

(57) ABSTRACT

The present invention relates to isolated polynucleotides and polypeptides encoded thereby that are useful for making transgenic plants. The transgenic plants produced have increased tolerance to cold, low temperature or chilling conditions. Such plants have a higher and/or faster germination rate, and produce more biomass compared to wild-type plants grown under the same cold, low temperature or chilling conditions.

15 Claims, 4 Drawing Sheets

Figure 1
Functional Homolog Table for Lead 83 – ME01451

| | | | | | | | |
|---|---|---|---|---|---|---|---|
| gi\|62526422 | MA----LSHPM | TFSLFLTFL | ALTAAQSPMM | APTMPPSTMS | MPP------ | | 40 |
| CeresClone:1606506 | MA----VSRYI | LLLSFTYLA | AFSTAQAPSM | SPM----MMP | MAPPPS---- | | 39 |
| Lead83-Clone-30087 | MASSFSSQAF | FLLTLSMVLI | PFSLAQAPMM | APS----GSMS | MPPMSSGGGS | | 47 |
| CeresClone:947579 | MA----ASQAF | CLLTLSMALV | HFSLAQSPMM | APS----GSMS | MPPMPSGGS- | | 43 |
| Consensus | MA-----SQA- | -LLTL-M-L- | AFSLAQ-PMM | APS----GSMS | MPPMPSGG-- | | 50 |

| | | | | | | | |
|---|---|---|---|---|---|---|---|
| gi\|62526422 | --TTSTTTPP | P-MSSMSPP- | PSAMSPTP-- | STMSPPPMS- | ----PMTPSMS | | 80 |
| CeresClone:1606506 | ---TMPMTPPP | STMPMTPPPT | PMTMTPPPMM | MPMTPPPMPM | GTPPMTMPMG | | 87 |
| Lead83-Clone-30087 | SVPPPVMS--- | P-MPMMTPP- | PMPMTPSP-- | MPMTPPPMPM | APPPMPMASP | | 91 |
| CeresClone:947579 | ---PMPMMTPP | P-MPMMTPP- | PMAMAPPP-- | MPMTPPPMPM | APMPMTPSSS | | 87 |
| Consensus | ---MPM-TPP | P-MPMMTPP- | PMAMTP-P-- | MPMTPPPMPM | APPPMT-S-S | | 100 |

| | | | | | | | |
|---|---|---|---|---|---|---|---|
| gi\|62526422 | PMGPMTPTMS | PM-----DSP | PAPAGPGMAP | GMSTPGP--- | APGPMGGESM | | 122 |
| CeresClone:1606506 | PLPPMMMPMS | PGPSMMPASP | PSPMGPSMA- | -----PEPATM | SPGPSMTPAF | | 130 |
| Lead83-Clone-30087 | PMMPMTPSTS | PSPLFVPDMP | SPPMPSGME- | -----SSP--- | SPGP-MPPAM | | 132 |
| CeresClone:947579 | PMSPPTFTMA | PSPEFVPDMA | SPPMMPGME- | -----SSP--- | SPGP-MPPAM | | 127 |
| Consensus | PM-PMTPTMS | PSP-TVPD-P | ---PMGPGM-- | ------SP---- | SPGP-MPPAM | | 150 |

| | | | | |
|---|---|---|---|---|
| gi\|62526422 | ASPFPSSGFV | HGISTSMAMV | ---ATGSVAL | FF | 152 |
| CeresClone:1606506 | -ETPASGAL M | QYSSITMLG | --------V | | 150 |
| Lead83-Clone-30087 | AASPDSGAFN | VRNNVVFLSC | YVGVVAAHFL | LV | 164 |
| CeresClone:947579 | -ASPDSGAFN | VRNDVVAL SF | ---LVAAHLL | LV | 155 |
| Consensus | AASPDSGAF- | VRNS--NLS- | -----VAAH-L | LV | 162 |

Figure 2
Functional Homolog Table for Lead 84 – ME02779

```
gi|14701800                    MALVEGNNGV SGGAVSFSEE QEALVLKSWA I MKKDSAN G LRFFLKIFEV   50
CeresClone:1554560             ----MALAEA DDGAVVFGEE QEALVLKSWA VMKKDAANLG LRFFLKVFEI   46
CeresClone:839727              --------MSA AEGAVVFSEE KEALVLKSWA I MKKDSANLG LRFFLKIFEI   43
gi|30909306                    --------ME SEGKI VFTEE QEALVVKSWS VMKKNSADLG LKLFIKIFEI   42
Lead84-clone30469-ME02779-trun --------ME SEGKI VFTEE QEALVVKSWS VMKKNSAELG LKLFIKIFEI   42
Lead84-full                    --------ME SEGKL VFTEE QEALVVKSWS VMKKNSAELG LKLFIKIFEI   42
gi|12963875                    ----------- ---MSSFSEE QEALVVKSWG SMKKDAGEMG LKFFLKIFEI   37
gi|37903656                    ----------- -MEGKVFTEE QETLVVKSWG VMKKNAAELG LKFFLKIFEI   39
gi|15824736                    --------MA TYEGKVFTEE QEALVVKSWT VMKKKTAELG LKFFLKIFEI   42
CeresClone:546001              --------MT TTLERGFSEE QEALVVKSWN VMKKNSGELG LKFFLKIFEI   42
gi|11095158                    --------MG TLDTKGFTEE QEALVVKSWN AMKKNSAELG LKLFLKIFEI   42

Consensus                      --------M- S-G--VFTEE QEALVVKSW- VMKKNSAELG LKFFLKIFEI   50 gi|14701800                    APSASQMFSF LRNSDVPLEK NPKLKT HAMS VFVMTCEAAA QLRKAGKVTV   100
CeresClone:1554560             APSAKQMFSF LRDSDVPLEK NPKLKT CEAA VFVMTCEAAA QLRKAGKVTV    96
CeresClone:839727              APSARQMFPF LRDSDVPLET NPKLKT HAVS VFVMTCEAAA QLRKAGKI TV    93
gi|30909306                    APTAKKLFSF LRDSPI PAEQ NPKLKPHAMS VFVMCCESAA QLRKI TGKVTV    92
Lead84-clone30469-ME02779-trun APTT KKMFSF LRDSPI PAEQ NPKLKPHAMS VFVM------- ----------    76
Lead84-full                    APTT KKMFSF LRDSPI PAEQ NPKLKPHAMS VFVMCCESAV QLRKI TGKVTV    92
gi|12963875                    APSAKKMFSF LKDSNVPLDQ NPKLKI HAKS VLVMTCEAAV QLRKAGKVVV    87
gi|37903656                    APSAQKLFSF LRDSDI PLEK NPKLKPHAMS VFVMTCESAV QLRKAGKVTV    89
gi|15824736                    APSAKKLFSF LRDSNVPLEQ NT KLKPHAMS VFVMTCESAV QLRKAGKVTV    92
CeresClone:546001              APSAQKLFSF LRDST VPLEQ NPKLKPHAVS VFVMTCDSAV QLRKAGKVTV    92
gi|11095158                    APSAQKLFSF LKDSKVPLEQ NT KLKPHAMS VFLMTCESAV QLRKSGKVTV    92

Consensus                      APSAKKMFSF LRDSDVPLEQ NPKLKPHAMS VFVMTCESAV QLRKAGKVTV   100 gi|14701800                    RDTTLKRLGA THFKYGVCDA HFEVTRFALL ETI KEAVPVD MWSPAMKSAW   150
CeresClone:1554560             RETTLKRLGA THLRYGVADG HFEVTGFALL ETI KEALPAD MWSLEMKKAW   146
CeresClone:839727              RETTLKRLGG THLKYGVADG HFEVTRFALL ETI KEALPAD MWGPEMRNAW   143
gi|30909306                    KETTLKRLGA NHSKYGVVDE HFEVTKYALL ETI KEAVP-E MWSPEMKSAW   141
Lead84-clone30469-ME02779-trun ---------- ---------- ---------- ---------- ----------    76
Lead84-full                    RETTLKRLGA SHSKYGVVDE HFEVAKYALL ETI KEAVP-E MWSPEMKVAW   141
gi|12963875                    RDSTLKKI GA THFKYGVVDE HFEVTKYALL ETI KEASQ-E MWSVEMKNAW   136
gi|37903656                    RESTLKRLGG VHFKSCVVDE HYEVTKFALL ETI KEALP-E MWSPEMKNAW   138
gi|15824736                    RESNLKKLGA THFKYGVVDE HFEVTKFALL ETI KEAVP-D MWSDEMKNAW   141
CeresClone:546001              RESNLKKLGA THFRT GVANE HFEVTKFALL ETI KEAVP-E MWSPAMKNAW   141
gi|11095158                    RESSLKKLGA NHFKYGVVDE HFEVTKFALL ETI KEAVP-E MWSPAMKNAW   141

Consensus                      RE-TLKRLGA THFKYGVVDE HFEVTKFALL ETI KEAVP-E MWSPEMKNAW   150 gi|14701800                    SEAYNQLVAA I KQEMKPAE- --   169
CeresClone:1554560             AEAYSQLVAA I KREMKPDA- --   165
CeresClone:839727              GEAYDQLVAA I KQEMKPSE- --   162
gi|30909306                    GQAYDHLVAA I KAEMKPSH- --   160
Lead84-clone30469-ME02779-trun ---YN----- ---------- --    78
Lead84-full                    GQAYDHLVAA I KAEMNLSN- --   160
gi|12963875                    GEAYDQLVSA I KTEMK---- --   152
gi|37903656                    GEAYDQLVAA I KSEMKPPLN --   158
gi|15824736                    GEAYDRLVAA I KI EMKACSQ AA   163
CeresClone:546001              GEAYDQLVDA I KSEMKPPSS --   161
gi|11095158                    GEAYDQLVNA I KSEMKPSS- --   160

Consensus                      GEAYDQLVAA I KSEMKP--- --   172
```

Figure 3
Functional Homolog Table for Lead 86 – ME03944

| | | | | | | |
|---|---|---|---|---|---|---|
| CeresClone:36046 | MAKRTKKVGI | VGKYGTRYGA | SIRKQIKKME | VSQHSKYFCE | FCGKXGVKXK | 50 |
| Lead86-Clone-271822 | MAKRTKKVGI | VGKYGTRYGA | SIRKQIKKME | VSQHSKYFCE | FCGKYGVKRK | 50 |
| gi\|6016699 | MTKRTKKARI | VGKYGTRYGA | SLRKQIKKME | VSQHNKYFCE | FCGKYSVKRK | 50 |
| CeresClone:858438 | MTKRTKKAGI | VGKYGTRYGA | SLRKQIKKME | VSQHSKYFCE | FCGKFAVKRK | 50 |
| CeresClone:832613 | MTKRTKKAGI | VGKYGTRYGA | SLRKQIKKME | VSQHSKYFCE | FCGKFAVKRK | 50 |
| CeresClone:1390976 | MTKRTKKAGI | VGKYGTRYGA | SLRKQIKKME | VSQHSKYFCE | FCGKFAVKRK | 50 |
| CeresClone:1457185 | MTKRTKKAGI | VGKYGTRYGA | SLRKQIKKME | VSQHSKYFCE | FCGKFAVKRK | 50 |
| gi\|56202147 | MTKRTKKAGI | VGKYGTRYGA | SLRKQIKKME | VSQHSKYFCE | FCGKFAVKRK | 50 |
| gi\|4741896 | MTKRTKKAGI | VGKYGTRYGA | SLRKQIKKME | VSQHSKYFCE | FCGKYAVKRK | 50 |
| gi\|4090257 | MTKRTKKAGI | VGKYGTRYGA | SLRKQIKKME | VSQHSKFFCE | FCGKFAVKRK | 50 |
| gi\|58578274 | MTKRTKKAGI | VGKYGTRYGA | SLRKQIKKME | VSQHSEYFCE | FCGKYAVKRK | 50 |
| CeresClone:664936 | MTKRTKKAGI | VGKYGTRYGA | SLRKQIKKME | VSQHSKFFCE | FCGKYAVKRK | 50 |
| CeresClone:1049262 | MTKRTKKAGI | VGKYGTRYGA | SLRKQIKKME | VSQHSKFFCE | FCGKYAVKRK | 50 |
| Consensus | MTKRTKKAGI | VGKYGTRYGA | SLRKQIKKME | VSQHSKYFCE | FCGK-AVKRK | 50 |

| | | | | | | |
|---|---|---|---|---|---|---|
| CeresClone:36046 | AVGIWGCKDC | GKVKAGGAYT | MNTASAVTVR | STIRRLREQ | EG | 92 |
| Lead86-Clone-271822 | AVGIWGCKDC | GKVKAGGAYT | MNTASAVTVR | STIRRLREQ | EG | 92 |
| gi\|6016699 | VVGIWGCKDC | GKVKAGGAYT | MNTASAVTVR | STIRRLREQT | ES | 92 |
| CeresClone:858438 | AVGIWGCKDC | GKVKAGGAYT | MNTASAVTVR | STIRRLREQT | EA | 92 |
| CeresClone:832613 | AVGIWGCKDC | GKVKAGGAYT | MNTASAVTVR | STIRRLREQT | EA | 92 |
| CeresClone:1390976 | AVGIWGCKDC | GKVKAGGAYT | MNTASAVTVR | STIRRLREQT | EA | 92 |
| CeresClone:1457185 | AVGIWGCKDC | GKVKAGGAYT | MNTASAVTVR | STIRRLREQT | EA | 92 |
| gi\|56202147 | AVGIWGCKDC | GKVKAGGAYT | MNTASAVTVR | STIRRLREQT | EA | 92 |
| gi\|4741896 | AVGIWCCKAC | GKVKAGGAYT | LNTASAVTVR | STIRRLREQT | ES | 92 |
| gi\|4090257 | AVGIWGCKDC | GKVKAGGAYT | LNTPSAVTVR | STIRRLREQT | EG | 92 |
| gi\|58578274 | AVGIWGCKDC | GKVKAGGAYT | LNTASAVTVR | STIRRLREQT | ES | 92 |
| CeresClone:664936 | AVGIWGCKDC | GKVKAGGAYT | LNTASAVTVR | STIRRLREQT | EG | 92 |
| CeresClone:1049262 | AVGIWGCKDC | GKVKAGGAYT | LNTASAVTVR | STIRRLREQT | ES | 92 |
| Consensus | AVGIWGCKDC | GKVKAGGAYT | MNTASAVTVR | STIRRLREQT | EA | 92 |

Figure 4
Functional Homolog Table for Lead 87 – ME05304

| | | | | | | |
|---|---|---|---|---|---|---|
| CeresClone:513071 | MQIFVKTLTG | KTITLEVESS | DTVDNVKAKI | QDKEGIPPDQ | QRLIFAGKQL | 50 |
| CeresClone:1482731 | MQIFVKTLTG | KTITLEVESS | DTIDNVKSKI | QDKEGIPPDQ | QRLIFAGKQL | 50 |
| Lead87-full | MQIFVKTLTG | KTITLEVESS | DTIDNVKAKI | QDKEGIPPDQ | QRLIFAGKQL | 50 |
| CeresClone:522921 | MQIFVKTLTG | KTITLEVESS | DTIDNVKAKI | QDKEGIPPDQ | QRLIFAGKQL | 50 |
| CeresClone:1036726 | MQIFVKTLTG | KTITLEVESS | DTIDNVKAKI | QDKEGIPPDQ | QRLIFAGKQL | 50 |
| Lead87-Clone2403-ME05304-Trunc | MQIFVKTLTG | KTITLEVESS | DTIDNVKAKI | QDK------ | ---------- | 33 |
| Consensus | MQIFVKTLTG | KTITLEVESS | DTIDNVKAKI | QDKEGIPPDQ | QRLIFAGKQL | 50 |

| | | | | | | |
|---|---|---|---|---|---|---|
| CeresClone:513071 | EDGRTLADYN | IQKESTLHLV | LRLRGGTMIK | VKTLTGKEIE | IDIEPTDTID | 100 |
| CeresClone:1482731 | EDGRTLADYN | IQKESTLHLV | LRLRGGTMIK | VKTLTGKEIE | IDIEPTDTID | 100 |
| Lead87-full | EDGRTLADYN | IQKESTLHLV | LRLRGGTMIK | VKTLTGKEIE | IDIEPTDTID | 100 |
| CeresClone:522921 | EDGRTLADYN | IQKESTLHLV | LRLRGGTMIK | VKTLTGKEIE | IDIEPTDTID | 100 |
| CeresClone:1036726 | EDGRTLADYN | IQKESTLHLV | LRLRGGTMIK | VKTLTGKEIE | IDIEPTDTID | 100 |
| Lead87-Clone2403-ME05304-Trunc | ---------- | ---------- | ---------- | ---------- | ---------- | 33 |
| Consensus | EDGRTLADYN | IQKESTLHLV | LRLRGGTMIK | VKTLTGKEIE | IDIEPTDTID | 100 |

| | | | | | | |
|---|---|---|---|---|---|---|
| CeresClone:513071 | RIKERVEEKE | GIPPVQQRLI | YAGKQLADDK | TAKDYNIEGG | SVLHLXLALR | 150 |
| CeresClone:1482731 | RIKERVEEKE | GIPPVQQRLI | YAGKQLADDK | TAKDYNIEGG | SVLHLVLALR | 150 |
| Lead87-full | RIKERVEEKE | GIPPVQQRLI | YAGKQLADDK | TAKDYAIEGG | SVLHLVLALR | 150 |
| CeresClone:522921 | RIKERVEEKE | GIPPVQQRLI | YAGKQLADDK | TAKEYNIEGG | SVLHLVLALR | 150 |
| CeresClone:1036726 | RIKERVEEKE | GIPPVQQRLI | YAGKQLADDK | TXKDYNIEGG | SVSA------ | 144 |
| Lead87-Clone2403-ME05304-Trunc | ---------- | ---------- | ---------- | ---------- | ---------- | 33 |
| Consensus | RIKERVEEKE | GIPPVQQRLI | YAGKQLADDK | TAKDYNIEGG | SVLHLVLALR | 150 |

| | | |
|---|---|---|
| CeresClone:513071 | GGY- | 153 |
| CeresClone:1482731 | GGSD | 154 |
| Lead87-full | GGLL | 154 |
| CeresClone:522921 | GGTY | 154 |
| CeresClone:1036726 | SGS- | 147 |
| Lead87-Clone2403-ME05304-Trunc | ---- | 33 |
| Consensus | GGS- | 154 |

Figure 5
Functional Homolog Table for Lead 105 – ME03186

```
CeresClone:1055099      MRKARPPQPQ PQP-------  SQQSPEIRYR GVRKRPSGRY AAEIRDPAKK    43
CeresClone:273307       MRR-RGVAAA DA--------  DGDV-ELRFR GVRKRPWGRY AAEIRDPAKK    40
Lead-ME03186b           MCRG-GTAAA AAEVAEPGLR PVYFKEQRYR GVRKRPWGRF AAEIRDPLKK    49
gi|12322345             MRRGRGSSAV AGPTVVAAI- NGSVKEIRFR GVRKRPWGRF AAEIRDPWKK    49
CeresClone:975672       MRKGRGSSAV PPAL------ PGSVKEPRYR GVRKRPWGRF AAEIRDPLKK    44

Consensus               MRRGRGT-A- ---------- -G-VKEIRYR GVRKRPWGRF AAEIRDP-KK    50

CeresClone:1055099      TPIWLGTFDC AEDAARAYDS AARSLRGPIA RTNFPPSSAT QPPPR-----    88
CeresClone:273307       ARVWLGTFDS AEDAARAYDA AARMLRGPKA RTNFPLPAAA ALHHP----H    86
Lead-ME03186b           ARVWLGTFDT AEEAARAYDT AARILRGPKA KTNFPL---- SPPFY-----    90
gi|12322345             ARVWLGTFDS AEEAARAYDS AARNLRGPKA KTNFPIDSSS PPPPNLRFNQ    99
CeresClone:975672       SRVWLGTFDS AEEAARAYDA AARNLRGPKA KTNFPIDCSP SSPLQ-----    89

Consensus               ARVWLGTFDS AEEAARAYD- AAR-LRGPKA KTNFP--S-- SPP-------   100

CeresClone:1055099      ------PPP  PI-------- ------AAAAA AATSSQSSTV ESWSGGGPRA   117
CeresClone:273307       MPAAAAAAAP PYIIYPTATG -VVSTPPVAR PACSSLSSTV ESFSGARPR-   134
Lead-ME03186b           ------HPD  PFSDHRHFAN TGEDFHDHRR PTSSCMSSTV ESFSCPRAAV   133
gi|12322345             IRNQNQNQVD PFMDHRLFTD HQQQFPIVNR PISSSMSSTV ESFSGPRP--   147
CeresClone:975672       -PLHHRNQID PFMDHRLYGG -EQEVVIISR PASSSMSSTV KSCSGVRPAS   137

Consensus               ---------D PF-DHR-F-- --Q-----V-R PASSSMSSTV ESFSG-RP--   150

CeresClone:1055099      PARARSAA-- -RAGIAKEGE E-DCRSVCCS SSSVLLEEGA DDAAASL---R  160
CeresClone:273307       PVLPPI---- RFPI-PPSIP DGDCRSDCCS SASVL-VDDDC TDAAASASCP   176
Lead-ME03186b           PATAPVATGR RYPRTPPVIP E-DCRSDCDS SSSV-VDDGE GDNVASSFPR   181
gi|12322345             TTMKPATI-K RYPRTPPVVP E-DCHSDCDS SSSV-DDDD DIASSSRRRN    194
CeresClone:975672       SSVAKAAT-K RYPRTPPVAP E-DCRSDCDS SSSV-VEDGX DIASSSSRRK   184

Consensus               P--APAAT-K RYPRTPPVVP E-DCRSDCDS SSSV-VDDG- DDA-ASS--R   200

CeresClone:1055099      SPLPFDLNMP PPQEGA----  LDAEADMIG  RYDILLRL              194
CeresClone:273307       FPLPFDLNLP PGGGAGVGF  YADEEDELRL  ---TALRL              211
Lead-ME03186b           EPLPFDLNAL PLDDAD----  ---VATDDLFC ---TVLCL              210
gi|12322345             PPFQFDLNFP PLDCVD----  LFNGADDLHC  ---TDLRL              225
CeresClone:975672       PPFEFDLNFX PLDCVD----  LFVGADDXXC  ---TDLRL              215

Consensus               -PLPFDLN-P PLD--D----  L----ADDL-C ---T-LRL              238
```

NUCLEOTIDE SEQUENCES AND POLYPEPTIDES ENCODED THEREBY USEFUL FOR MODIFYING PLANT CHARACTERISTICS IN RESPONSE TO COLD

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., T T Kozlowsky, ed, Academic Press, New York, pp 23–64; Graham and Patterson (1982) *Annu Rev Plant Physiol* 33: 347–372; Guy (1990) *Annu Rev Plant Physiol Plant Mol Biol* 41:187–223; and Nishida and Murata (1996) *Annu Rev Plant Physiol Plant Mol Biol* 47: 541–568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1—Functional Homolog Table for Lead 83—ME01451 (SEQ ID NO:2). Alignment of Lead 83 with homologs gi62526422 (SEQ ID NO:4), CeresClone: 1606506 (SEQ ID NO:5), and CeresClone: 947579 (SEQ ID NO:3). Conserved regions are enclosed in a box. A consensus sequence is shown below the alignment.

FIG. 2—Functional Homolog Table for Lead 8—ME02779, truncated (SEQ ID NO:7) and full (SEQ ID NO:9). Alignment of Lead 8, full and truncated, with homologs gi14701800 (SEQ ID NO:18), CeresClone: 1554560 (SEQ ID NO:16). CeresClone: 839727 (SEQ ID NO:17), gi30909306 (SEQ ID NO:10), gi12963875 (SEQ ID NO:15), gi37903656 (SEQ ID NO:11), gi15284736 (SEQ ID NO:12). CeresClone: 546001 (SEQ ID NO:13) and gi1195158 (SEQ ID NO:14). Conserved regions are enclosed in a box. A consensus sequence is shown below the alignment.

FIG. 3—Functional Homolog Table for Lead 86—ME03944 (SEQ ID NO:20). Alignment of Lead 86 with homologs CeresClone: 36046 (SEQ ID NO:23), gi6016699 (SEQ ID NO: 24). CeresClone: 858438 (SEQ ID NO:26). CeresClone: 632613 (SEQ ID NO:24), CeresClone: 1390976 (SEQ ID NO:29), CeresClone: 1457185 (SEQ ID NO:30), gi56202147 (SEQ ID NO:31), gi4741896 (SEQ ID NO:22), gi4090257 (SEQ ID NO:21), gi58576274 (SEQ ID NO:32), CeresClone: 664936 (SEQ ID NO:25) and Ceres-Clone: 1049262 (SEQ ID NO:27). Conserved regions are enclosed in a box. A consensus sequence is shown below the alignment.

FIG. 4—Functional Homolog Table for Lead 87—ME05304, truncated (SEQ ID NO:40) and full (SEQ ID NO:34). Alignment of Lead 87, truncated and full, with homologs CeresClone: 513071 (SEQ ID NO:38), Ceres-Clone: 1482731 (SEQ ID NO:35), CeresClone: 522921 (SEQ ID NO:36) and CeresClone: 1036726 (SEQ ID NO:37). Conserved regions are enclosed in a box. A consensus sequence is shown below the alignment.

FIG. 5—Functional Homolog Table for Lead 105—ME03186 (SEQ ID NO:42). Alignment of Lead 105 with homologs CeresClone: 1055099 (SEQ ID NO:46). Ceres-Clone: 273307 (SEQ ID NO:45) gi12322345 (SEQ ID NO:43) and CeresClone: 975672 (SEQ ID NO:44). Conserved regions are enclosed in a box. A consensus sequence is shown below the alignment.

DETAILED DESCRIPTION OF THE INVENTION

1. Definitions

The following terms are utilized throughout this application:

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure and/or (3) three-dimensional conformation. Generally, each domain has been associated with either a family of proteins or motifs. Typically, these families and/or motifs have been correlated with specific in-vitro and/or in-vivo activities. A domain can be any length, including the entirety of the sequence of a protein. Detailed descriptions of the domains, associated families and motifs, and correlated activities of the polypeptides of the instant invention are described in the Sequence Listing. Usually, the polypeptides with designated domain(s) can exhibit at least one activity that is exhibited by any polypeptide that comprises the same domain(s).

Endogenous: The term "endogenous," within the context of the current invention refers to any polynucleotide, polypeptide or protein sequence which is a natural part of a cell or organism regenerated from said cell.

Exogenous: "Exogenous," as referred to within, is any polynucleotide, polypeptide or protein sequence, whether chimeric or not, that is initially or subsequently introduced into the genome of an individual host cell or the organism regenerated from said host cell by any means other than by a sexual cross. Examples of means by which this can be accomplished are described below and include *Agrobacterium*-mediated transformation (of dicots—e.g. Salomon et al. (1984) *EMBO J.* 3:141; Herrera-Estrella et al. (1983) *EMBO J.* 2:987; of monocots, representative papers are those by Escudero et al. (1996) *Plant J.* 10:355, Ishida et al. (1996) *Nature Biotechnology* 14:745, May et al. (1995) *Bio/Technology* 13:486), biolistic methods (Armaleo et al. (1990) *Current Genetics* 17:97), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50–60%;

even more typically between 70 to 80%; even more typically between 90 to 100% of the other.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an *Arabidopsis* gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Masterpool: The "master pools" discussed in these experiments are a pool of seeds from five independent transformation events of the same exogenous nucleotide sequence.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math.* 2:482, by the homology alignment algorithm of Needleman and Wunsch (1970) *J. Mol. Biol.* 48:443), by the search for similarity method of Pearson and Lipman (1988) *Proc. Natl. Acad. Sci.* (SA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol. Biol.* 30:321–9.); RCc2 and RCc3, promoters that direct root-specific gene transcription in rice (Xu et al. (1995) *Plant Mol. Biol.* 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$—5° C. to $T_m$—10° C. Medium or moderate stringency conditions are those providing $T_m$—20° C. to $T_m$—29° C. Low stringency conditions are those providing a condition of $T_m$—40° C. to $T_m$—48° C. The relationship of hybridization conditions to $T_m$ (in ° C.) is expressed in the mathematical equation $$T_m = 81.5 - 16.6(\log_{10}[Na^+]) + 0.41(\% \ G+C) - (600/N) \tag{1}$$

where N is the length of the probe. This equation works well for probes 14 to 70 nucleotides in length that are identical to the target sequence. The equation below for $T_m$ of DNA—DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% \ G+C) - 500/L 0.63(\% \ formamide) \tag{2}$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10–15° C. higher than calculated, for RNA—RNA hybrids $T_m$ is 20–25° C. higher. Because the $T_m$ decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5–8° C. below $T_m$, medium or moderate stringency is 26–29° C. below $T_m$ and low stringency is 45–48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

2. Important Characteristics of the Polynucleotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the farmer and, better yield under low temperatures.

3. The Genes of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

The polypeptides of the invention also include those comprising the consensus sequences described in FIGS. 1–5. Polypeptides comprised of a sequence within and defined by one of the consensus sequences can be utilized for the purposes of the invention, namely to make transgenic plants with improved tolerance to cold conditions.

4. Use of the Genes to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., Molecular Cloning: A Laboratory Manual, Second Edition, Cold Spring Harbor Laboratory Press, 1989, New York) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794–8797; Hamilton et al. (1996) *Proc. Natl. Acad. Sci. USA* 93: 9975–9979;

(b) YAC: Burke et al. (1987) *Science* 236:806–812;

(c) PAC: Sternberg N. et al. (1990) *Proc Natl Acad Sci USA*. *January;* 87:103–7;

(d) Bacteria-Yeast Shuttle Vectors: Bradshaw et al. (1995) *Nucl Acids Res* 23: 4850–4856;

(e) Lambda Phage Vectors: Replacement Vector, e.g., Frischauf et al. (1983) *J. Mol Biol* 170: 827–842; or Insertion vector, e.g., Huynh et al., In: *Glover N M* (ed) DNA Cloning: A practical Approach, Vol. 1 Oxford: IRL Press (1985); T-DNA gene fusion vectors: Walden et al. (1990) *Mol Cell Biol* 1: 175–194; and (g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica*, v. 85, n.1–3:13–27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention: Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2–5, 7, 9–18, 20–32, 34–38, 40 and 42–46 due to the fact that the different nucleic acid sequence encodes a protein having one or more conservative amino acid changes.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Identification of Useful Nucleotide Sequences

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5×MS Media is prepared and the pH adjusted to 5.7 using ION KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 µEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

REFERENCES

Levitt (1980) Chilling injury and resistance. In T T Kozlowsky, ed, Chilling, Freezing, and High Temperature Stresses: Responses of Plant to Environmental Stresses, Vol 1. Academic Press, New York, pp 23–64.

Graham and Patterson (1982) *Annu Rev Plant Physiol* 33: 347–372.

Guy (1990) *Annu Rev Plant Physiol Plant Mol Biol* 41: 187–223.

Nishida and Murata (1996) *Annu Rev Plant Physiol Plant Mol Biol* 47: 541–568.

EXAMPLES

Summary

| | |
|---|---|
| Trait area(s) | Cold |
| Sub-trait Area | Cold - germination and vigor |
| Coding sequence/ Species of Origin | 1. Vector Construct Sequence Identifier 14298746 corresponding to Clone 30087 - ME01451; encodes a 164 amino acid protein of unknown function from Arabidopsis. |
| | 2. Vector Construct Sequence identifier 14298770 corresponding to Clone 30469 - ME02779 encodes a 78 amino acid protein with identity to the N-terminal half of an Arabidopsis class I nonsymbiotic hemoglobin. |
| | 3. Vector Construct Sequence Identifier 14301197 corresponding to Clone 271922 - ME03944 encodes a 92 amino acid 60s ribosomal protein L37a protein from Arabidopsis. |
| | 4. Vector Construct Sequence Identifier 14296769 corresponding to Clone 2403 - ME05304 encodes a truncated ubiquitin-like protein from Arabidopsis. |
| | 5. Vector Construct Sequence Identifier 14301334 corresponding to Clone 674166 - ME03186 from *Glycine max* encodes a 210 amino acid protein with similarity to the ethylene-responsive element binding protein (ERF) family. |
| Species in which Clone was Tested | *Arabidopsis thaliana* |
| Promoter | 35S, a strong constitutive promoter |
| Insert DNA type | cDNA |

Introduction:

How plants respond to stress in the environment dictates their ability to survive and reproduce. There are probably many mechanisms by which plants regulate the temperatures under which they will germinate (Lu and Hills, 2003). Finding genes that result in stress tolerance when over-expressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods:

Generation and Phenotypic Evaluation of $T_1$ Events.

Wild-type *Arabidopsis* Wassilewskija (Ws) plants were transformed with a Ti plasmid containing different Clones in the sense orientation relative to the 35S promoter, by *Agrobacterium*-Mediated Transformation. The Ti plasmid vector used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.

in the second and third generations and 3) determining the lack of significant negative phenotypes.

1. Superpools screened for Cold Germination
2. Cold tolerant candidates identified
3. Independent events tested for Cold Germination and Finale™ resistance in two generations
4. For all leads, at least 2 Events were significantly tolerant to cold in 2 generations
5. Tested positive events for negative phenotypes Growth Conditions and Planting Schema Under cold Germination.

Up to five independent $T_2$ transformation events were evaluated for each line under cold conditions. Subsequently, $T_3$ generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5×MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

Results:

Example 1

Lead 83—ME01451

TABLE 1-1

| Construct | Event/Generation | Plant Stage | Assay | Result |
| --- | --- | --- | --- | --- |
| 35S::30087 | -01/$T_2$ Finale resistant plants | Seedling | Cold Germination | Significant at p ≦ .05 |
| 35S::30087 | -05/$T_2$ Finale resistant plants | Seedling | Cold Germination | Significant at p ≦ .05 |
| 35S::30087 | -01/$T_3$ Finale resistant plants | Seedling | Cold Germination | Significant at p ≦ .05 |
| 35S::30087 | -05/$T_3$ Finale resistant plants | Seedling | Cold Germination | Significant at p ≦ .05 |

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:

Procedure for 1) identifying the candidate from a cold germination superpool screen, 2) confirming the phenotype Ectopic expression of Clone 30087 under the control of the 35S promoter induces the following phenotypes:

Early germination at 8° C. resulting in larger seedlings after 10 days of growth in the cold.

Plants from Events -01 and -05 which are heterozygous or homozygous for Clone 30087 do not show any negative phenotypes under long-day conditions.

The gene corresponding to Clone 30087 is up-regulated in developing seedlings, seeds and siliques and down-regulated in drought, heat and ABA.

Two events of ME01451 showed significant early germination under cold conditions in both generations.

All five events of ME01451 were sown as described in the Cold Germination Assay in both the $T_2$ and the $T_3$ generations. Two events, -01 and -05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two events of ME01451 show 3:1 and 15:1 segregation for Finale™ resistance.

Events -01 and -05 segregated 15:1 and 3:1 (R:S), respectively, for Finale™ resistance in the $T_2$ generation (data not shown).

Qualitative analysis of the $T_1$ plants:
  The physical appearance of all ten $T_1$ plants was identical to the controls.

Qualitative and quantitative analysis of the $T_2$ plants:
  Events -01 and -05 of ME01451 exhibited no statistically relevant negative phenotypes.
    Germination
      No detectable reduction in germination rate.
    General morphology/architecture
      Plants appeared wild-type in all instances.
    Days to flowering
      No observable or statistical differences between experimentals and controls.
    Rosette area 7 days post-bolting
      No observable or statistical differences between experimentals and controls.
    Fertility (silique number and seed fill)
      No observable or statistical differences between experimentals and controls Ectopic expression of Clone 30469 under the control of the 35S promoter induces the following phenotypes:
  Early germination at 8° C. resulting in larger seedlings after 10 days at 8° C.

Plants from Events -01 and -03 which are heterozygous or homozygous for Clone 30469 do not show any negative phenotypes under long-day conditions.

The gene corresponding to Clone 30469 is down-regulated in ABA, heat, and germinating seeds and up-regulated in high nitrogen and most cold and drought treatments.

Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.

Two events of ME02779 showed significant early germination under cold conditions in both generations.

Five events of ME02779 were sown as described in the Cold Germination Assay in both the $T_2$ and the $T_3$ generations. Two events, -01 and -03 were significant in both generations at p=0.05 using a one-tailed t-test assuming unequal variance (Table 2-2). ME02779 transgenic seedlings were significantly larger than the pooled non-transgenic segregants.

Example 2

Lead 84—ME02779

TABLE 2-1

| Construct | Event/Generation | Plant Stage | Assay | Result |
|---|---|---|---|---|
| 35S::30469 | –01/$T_2$ Finale resistant plants | Seedling | Cold Germination | Significant at p ≦ .05 |
| 35S::30469 | –03/$T_2$ Finale resistant plants | Seedling | Cold Germination | Significant at p ≦ .05 |
| 35S::30469 | –01/$T_3$ Finale resistant plants | Seedling | Cold Germination | Significant at p ≦ .05 |
| 35S::30469 | –03/$T_3$ Finale resistant plants | Seedling | Cold Germination | Significant at p ≦ .05 |

TABLE 2-2

T-test comparison of seedling area between transgenic seedlings and pooled non-transgenic segregants after 10 days at 8° C.

| Line | Events | Transgenic | | | Pooled Non-Transgenics | | | t-test |
|------|--------|------|------|----|------|------|----|---------|
|      |        | Avg  | SE   | N  | Avg  | SE   | N  | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two events of ME02779 show 3:1 segregation for Finale™ resistance.

Events -01 and -03 segregated 3:1 (R:S) for Finale™ resistance in the $T_2$ generation (data not shown).

Qualitative analysis of the $T_1$ plants:
The physical appearance of nine of the ten $T_1$ plants was identical to the controls except for Event -09, which exhibited small rosettes and reduced fertility.

Qualitative and quantitative analysis of the $T_2$ plants:
Events -01 and -03 of ME02779 exhibited no statistically relevant negative phenotypes.

Germination
No detectable reduction in germination rate.

General morphology/architecture
Plants appeared wild-type in all instances.

Days to flowering
No observable or statistical differences between experimentals and controls.

Rosette area 7 days post-bolting
No observable or statistical differences between experimentals and controls.

Fertility (silique number and seed fill)
No observable or statistical differences between experimentals and controls Ectopic expression of Clone 271922 under the control of the 35S promoter induces the following phenotypes:

Early germination at 8° C. resulting in larger seedlings after 10 days at 8° C.

Plants from Events -02 and -06 which are heterozygous or homozygous for Clone 271922 do not show any negative phenotypes under long-day conditions.

The gene corresponding to Clone 271922 shows little differential regulation in transcription profiling experiments on wildtype.

Clone 271922 encodes a 60s ribosomal protein L37a.

Two events of ME03944 showed significant early germination under cold conditions in both generations.

Four events of ME03944 were sown as described in the Cold Germination Assay in both the $T_2$ and the $T_3$ generations. Two events, -02 and -06, were significant in both generations at $p \leq 0.05$ using a one-tailed t-test assuming unequal variance (Table 3-2). The $T_3$ lines are indicated as -99 which indicates that the seeds are the bulked progeny from several $T_2$ plants. ME03944 transgenic seedlings were significantly larger than the pooled non-transgenic segregants.

Example 3

Lead 86—ME03944

TABLE 3-1

| Construct | Event/Generation | Plant Stage | Assay | Result |
|-----------|------------------|-------------|-------|--------|
| 35S::271922 | -02/$T_2$ Finale resistant plants | Seedling | Cold Germination | Significant at $p \leq .05$ |
| 35S::271922 | -06/$T_2$ Finale resistant plants | Seedling | Cold Germination | Significant at $p \leq .05$ |
| 35S::271922 | -02/$T_3$ Finale resistant plants | Seedling | Cold Germination | Significant at $p \leq .05$ |
| 35S::271922 | -06/$T_3$ Finale resistant plants | Seedling | Cold Germination | Significant at $p \leq .05$ |

TABLE 3-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME03944 | ME03944-02 | 0.0115 | 0.0004 | 23 | 0.0069 | 0.0006 | 35 | 3.4023E−08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E−05 |
| ME03944 | ME03944-06-99 | 0.0077 | 0.0007 | 21 | 0.0051 | 0.0004 | 29 | 0.0011 |

Two events of ME03944 show 3:1 segregation for Finale™ resistance.

Events -02 and -06 segregated 3:1 (R:S) for Finale™ resistance in the $T_2$ generation (data not shown).

Qualitative analysis of the $T_1$ plants:
 The physical appearance of five of the six $T_1$ plants was identical to the controls. Event -03 exhibited a small rosette and curled leaves.

Other Characteristics:
 Seedlings from ME03944-06 exhibited elongated hypocotyls. This phenotype co-segregated with Finale™ resistance.

Qualitative and quantitative analysis of the $T_2$ plants:
 Events -02 and -06 of ME03944 exhibited no statistically relevant negative phenotypes.

Germination
  No detectable reduction in germination rate.

General morphology/architecture
  Plants appeared wild-type in all instances.

Days to flowering
  No observable or statistical differences between experimentals and controls.

Rosette area 7 days post-bolting
  No observable or statistical differences between experimentals and controls.
 Fertility (silique number and seed fill)
  No observable or statistical differences between experimentals and controls

Example 4

Lead 87—ME05304

Ectopic expression of Clone 2403 under the control of the 35S promoter induces the following phenotypes:

Early germination at 8° C. resulting in larger seedlings after 10 days at 8° C.

Plants from Events -01 and -04 which are heterozygous or homozygous for Clone 2403 do not show any negative phenotypes under long-day conditions.

The gene corresponding to Clone 2403 shows little differential regulation in transcript profiling experiments on wildtype.

Clone 2403 encodes a truncated ubiquitin-like protein.

Two events of ME05304 showed significant early germination under cold conditions in both generations.

Four events of ME05304 were sown as described in the Cold Germination Assay in both the $T_2$ and the $T_3$ generations. Two events, -01 and -04 were significant in both generations at $p \leq 0.05$ using a one-tailed t-test assuming unequal variance (Table 4-2). The $T_3$ lines are indicated as -99 which indicates that the seeds are the bulked progeny from several $T_2$ plants.

TABLE 4-1

| Construct | Event/Generation | Plant Stage | Assay | Result |
|---|---|---|---|---|
| 35S::2403 | -01/$T_2$ Finale resistant plants | Seedling | Cold Germination | Significant at $p \leq .05$ |
| 35S::2403 | -04/$T_2$ Finale resistant plants | Seedling | Cold Germination | Significant at $p \leq .05$ |
| 35S::2403 | -01/$T_3$ Finale resistant plants | Seedling | Cold Germination | Significant at $p \leq .05$ |
| 35S::2403 | -04/$T_3$ Finale resistant plants | Seedling | Cold Germination | Significant at $p \leq .05$ |

TABLE 4-2

T-test comparison of seedling area between transgenic seedlings and pooled non-transgenic segregants after 10 days at 8° C.

| Line | Events | Transgenic | | | Pooled Non-Transgenics | | | t-test |
|---|---|---|---|---|---|---|---|---|
| | | Avg | SE | N | Avg | SE | N | p-value |
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two events of ME05304 show 3:1 segregation for Finale™ resistance.

Events -01 and -04 segregated 3:1 (R:S) for Finale™ resistance in the $T_2$ generation (data not shown).

Qualitative analysis of the $T_1$ plants:
The physical appearance of seven of the ten $T_1$ plants was identical to the controls. The other three events exhibited the following phenotypes: late flowering (Events -01, -02 and -08), dark green rosette leaves (Events -01 and -08) and shorter petioles (Events -02 and -08). Event -01 did not reproduce the late-flowering phenotype in the $T_2$ generation.

Qualitative and quantitative analysis of the $T_2$ plants:
Events -01 and -04 of ME05304 exhibited no statistically relevant negative phenotypes.

Germination
   No detectable reduction in germination rate.

General morphology/architecture
   Plants appeared wild-type in all instances.

Days to flowering
   No observable or statistical differences between experimentals and controls.

Rosette area 7 days post-bolting
   No observable or statistical differences between experimentals and controls.

Fertility (silique number and seed fill)
   No observable or statistical differences between experimentals and controls.

Ectopic expression of Clone 674166 under the control of the 35S promoter results in early germination at 8° C. resulting in larger seedlings after 10 days at 8° C.

Plants from Events -04 and -05 which are hemizygous or homozygous for Clone 674166 do not show any negative phenotypes under long-day conditions.

Two events of ME03186 showed significant early germination under cold conditions in both generations.

Two events, -04 and -05 were significant in two generations at $p \leq 0.05$ using a one-tailed t-test assuming unequal variance (Table 5-2). '-99' signifies that seeds were pooled from several plants.

Example 5

Lead 105—ME03186

TABLE 5-1

| Construct | Event/Generation | Plant Stage | Assay | Result |
|---|---|---|---|---|
| 35S::674166 | –04/$T_3$ Finale resistant plants | Seedling | Cold Germination | Significant at $p \leq .05$ |
| 35S::674166 | –04/$T_4$ Finale resistant plants | Seedling | Cold Germination | Significant at $p \leq .05$ |
| 35S::674166 | –05/$T_2$ Finale resistant plants | Seedling | Cold Germination | Significant at $p \leq .05$ |
| 35S::674166 | –05/$T_3$ Finale resistant plants | Seedling | Cold Germination | Significant at $p \leq .05$ |

TABLE 5-2

T-test comparison of seedling area between transgenic seedlings and control non-transgenic segregants after 10 days at 8° C.

| Events | Event-Gen | Transgenic | | | Control Non-Transgenics[a] | | | t-test p-value |
|---|---|---|---|---|---|---|---|---|
| | | Avg | SE | N | Avg | SE | N | |
| ME03186-04-99[b] | 04-T3 | 0.0045 | 0.0003 | 35 | 0.0030 | 0.0002 | 31 | 1.37E−05 |
| ME03186-04-99 | 04-T3 | 0.0092 | 0.0003 | 48 | 0.0051 | 0.0005 | 12 | 3.72E−10 |
| ME03186-04-99-03 | 04-T4 | 0.0107 | 0.0002 | 70 | 0.0083 | 0.0005 | 34 | 2.72E−05 |
| ME03186-04-99-04 | 04-T4 | 0.0120 | 0.0004 | 62 | 0.0083 | 0.0005 | 34 | 3.61E−08 |
| ME03186-04-99-07 | 04-T4 | 0.0107 | 0.0003 | 69 | 0.0083 | 0.0005 | 34 | 4.91E−05 |
| ME03186-04-99-08 | 04-T4 | 0.0110 | 0.0003 | 69 | 0.0083 | 0.0005 | 34 | 5.53E−06 |
| ME03186-05[b] | 05-T2 | 0.0051 | 0.0005 | 22 | 0.0038 | 0.0005 | 6 | 0.0332 |
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a]Transgenic seedlings were compared to non-transgenic segregants within a seed line except for the $T_4$ generation of Event-04. Since these seed lines were homozygous, they were compared to pooled non-transgenic segregants from another $T_4$ generation event that was grown in the same flat as the $T_4$ generation of Event -04.
[b]These events were sown twice. The first time was to identify ME03186 as a hit. They were repeated the second time with two generations to identify ME03186 as a lead.

Two events of ME03186 show 3:1 segregation for Finale™ resistance.

Event -05 segregated 3:1 (R:S) for Finale™ resistance in the $T_2$ generation. $T_2$ generation seed was not available for Event -04. However, the $T_3$ generation seeds that were pooled from several $T_2$ plants segregated approximately 2:1 in a manner consistent with a single insert (see Table 5-2).

Qualitative and quantitative analysis of the $T_2$ plants (screening for negative phenotypes):

Events -04 and -05 of ME03186 exhibited no statistically significant negative phenotypes.

Germination
  No detectable reduction in germination rate.

General morphology/architecture
  Plants appeared wild-type in all instances.
Days to flowering
  No observable or statistical differences between experimentals and controls.
Rosette area 7 days post-bolting

REFERENCES

Hunt et al, (2001) *Plant Mol Biol* 47: 677–692.
Lu and Hills (2002) *Plant Physiol.* 129:1352–8

What is claimed is:

1. An isolated nucleic acid molecule comprising: a) a nucleic acid having a nucleotide sequence which encodes an amino acid sequence and exhibiting at least 95% sequence identity to SEQ ID NO: 42 and which provides cold tolerance when expressed in a plant; b) a nucleic acid having a nucleotide sequence which is a full complement of the nucleotide sequence according to paragraph (a); a nucleic acid having a nucleotide sequence which encodes an amino acid sequence according to SEQ ID NO: 42; or (d) a nucleic acid having a nucleotide sequence which is a full complement of the nucleotide sequence according to paragraph (c).

2. The isolated nucleic acid molecule according to claim 1, which has the nucleotide sequence according to SEQ ID NO: 41.

3. The isolated nucleic acid molecule according to claim 1, wherein said encoded amino acid sequence has a sequence according to SEQ ID NO: 42.

4. A vector construct comprising:
   a) a first nucleic acid having a regulatory sequence causing transcription and/or translation in a plant; and
   b) a second nucleic acid having the sequence of the isolated nucleic acid molecule according to any one of claims 1–3;

wherein said first and second nucleic acids are operably linked and wherein said second nucleic acid is heterologous to any element in said vector construct.

5. The vector construct according to claim 4, wherein said first nucleic acid is native to said second nucleic acid.

6. The vector construct according to claim 4, wherein said first nucleic acid is heterologous to said second nucleic acid.

7. A bacteria or plant host cell comprising the isolated nucleic acid molecule according to any one of claims 1–3 wherein said nucleic acid molecule is flanked by at least one exogenous nucleotide sequence relative to said nucleic acid molecule.

8. A bacteria or plant host cell comprising the vector construct according to claim 4.

9. A method of introducing an isolated nucleic acid into a host cell comprising: a) providing the isolated nucleic acid molecule according to claim 1; and b) contacting said isolated nucleic acid with said host cell under conditions that permit insertion of said nucleic acid into said host cell.

10. A method of transforming a bacteria or plant host cell that comprises contacting the host cell with the vector construct according to claim 4 to insert said construct into said host cell to obtain a transformed cell.

11. A plant, plant cell, plant material or seed of a plant which comprises a nucleic acid molecule comprising a) a nucleic acid having a nucleotide sequence which encodes an amino acid sequence and exhibiting at least 95% sequence identity to SEQ ID NO: 42 and which provides cold tolerance when expressed in a plant; b) a nucleic acid having a nucleotide sequence which is a full complement of the nucleotide sequence according to paragraph (a); (c) a nucleic acid having a nucleotide sequence which encodes an amino acid sequence according to SEQ ID NO: 42; or (d) a nucleic acid having a nucleotide sequence which is a full complement of the nucleotide sequence according to paragraph (c) wherein said nucleic acid is exogenous or heterologous to said plant or plant cell.

12. A plant, plant cell, plant material or seed of a plant which comprises a vector construct comprising a first nucleic acid having a regulatory sequence causing transcription and/or translation in a plant and a second nucleic acid having the sequence of an isolated nucleic acid molecule comprising a) a nucleic acid having a nucleotide sequence which encodes an amino acid sequence and exhibiting at least 95% sequence identity to SEQ ID NO: 42 and which provides cold tolerance when expressed in a plant; b) a nucleic acid having a nucleotide which is a full complement of the nucleotide sequence according to paragraph (a); (c) a nucleic acid having a nucleotide sequence which encodes an amino acid sequence according to SEQ ID NO: 42; or (d) a nucleic acid having a nucleotide which is a full complement of the nucleotide sequence according to paragraph (c).

13. A plant that has been regenerated from the plant cell or seed according to claim 11.

14. A plant, plant cell, plant material or seed of a plant which comprises an expressible nucleic acid molecule that is exogenous or heterologous to said plant, plant cell or seed comprising a) a nucleic acid having a nucleotide sequence which encodes an amino acid sequence and exhibiting at least 95% sequence identity to SEQ ID NO: 42; b) a nucleic acid having a nucleotide sequence which is a full complement of the nucleotide sequence according to paragraph (a); or (c) a nucleic acid having a nucleotide sequence which encodes an amino acid sequence according to SEQ ID NO: 42; or (d) a nucleic acid having a nucleotide sequence which is a full complement of the nucleotide sequence according to paragraph (c), wherein said plant has improved cold tolerance as compared to a wild-type plant cultivated under the same conditions, and wherein said seed comprises said nucleic acid.

15. A transgenic plant having a polynucleotide construct comprising a cold tolerance nucleic acid sequence operably linked to a plant promoter so that the cold tolerance nucleic acid sequence is ectopically overexpressed in the transgenic plant, and the transgenic plant exhibits: i) faster rate of seedling growth, ii) higher tolerance to cold, iii) faster germination rate, or iv) greater germination rate than a progenitor plant which does not contain the polynucleotide construct, when the transgenic plant and the progenitor plant are cultivated under identical environmental conditions, wherein the cold tolerance nucleic acid sequence encodes the polypeptide set forth in SEQ ID NO: 42.

* * * * *

SEQUENCE LISTING

```
<160> NUMBER OF SEQ ID NOS: 46

<210> SEQ ID NO 1
<211> LENGTH: 828
<212> TYPE: DNA
<213> ORGANISM: Arabidopsis thaliana
<220> FEATURE:
<221> NAME/KEY: misc_feature
<222> LOCATION: (1)..(828)
<223> OTHER INFORMATION: Ceres CLONE ID no. 30087
<220> FEATURE:
<221> NAME/KEY: CDS
<222> LOCATION: (100)..(592)
<223> OTHER INFORMATION: Referenced by SEQ ID NO: 2

<400> SEQUENCE: 1 aactttctc tcccactctt tcttttacta ctctcacaca tatctctgtc tatatatcac      60
tttacataaa ccactattcc acacacaaac acacatagcc atggcctctt ctttctcttc     120
acaagccttc ttcttgctca cattgtctat ggttttaatt cctttctctt tagctcaagc     180
tcccatgatg gctccttctg gctcaatgtc catgccgcct atgtctagcg gcggtggaag     240
ctcggttcct cctccagtga tgtctccgat gccaatgatg actccaccac ctatgcctat     300
gactccatca cccatgccca tgactccacc acctatgcct atggctccac caccaatgcc     360
catggcttca ccaccaatga tgccaatgac tccatctaca agcccaagcc cattaacagt     420
```

```
tccggatatg ccttcgccgc cgatgccatc cggaatggaa tcttcacctt ctccaggacc      480
catgccaccg gcaatggcgg cttcgccgga ttcgggagct ttcaatgtta gaaacaacgt      540
cgtaacactt tcatgcgttg ttggagttgt tgcagctcat tttctcctcg tttgaaatga      600
ttattgaatt ggtcagcctc gatcgttttc ttgtaattta ctttcatatt tttttttccct     660 caaattatta gtggtcatca ttttataata tttgagtttg tgtttgatgt acgattcaga      720
catttgtttg cattatgtgc ttaataagtt tatcgttgac tctacttgaa gagagacttt      780
gtgtgtgatg taaatttctt ctatctatgg aacattgcat tcgtagcc                  828
```

```
<210> SEQ ID NO 2
<211> LENGTH: 164
<212> TYPE: PRT
<213> ORGANISM: Arabidopsis thaliana

<400> SEQUENCE: 2

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Val Met Ser Pro Met Pro Met Thr Pro Pro Pro
    50                  55                  60

Met Pro Met Thr Pro Ser Pro Met Pro Met Thr Pro Pro Pro Met Pro
65                  70                  75                  80

Met Ala Pro Pro Met Pro Met Ala Ser Pro Pro Met Met Pro Met
                85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val
```

```
<210> SEQ ID NO 3
<211> LENGTH: 155
<212> TYPE: PRT
<213> ORGANISM: Brassica napus
<220> FEATURE:
<221> NAME/KEY: misc_feature
<222> LOCATION: (1)..(155)
<223> OTHER INFORMATION: Ceres CLONE ID no. 947579

<400> SEQUENCE: 3

Met Ala Ala Ser Gln Ala Phe Leu Leu Leu Thr Leu Ser Met Ala Leu
1               5                   10                  15

Val His Phe Ser Leu Ala Gln Ser Pro Met Met Ala Pro Ser Gly Ser
            20                  25                  30

Met Ser Met Pro Pro Met Pro Ser Gly Gly Ser Pro Pro Met Met
        35                  40                  45

Thr Pro Pro Pro Met Pro Met Thr Pro Pro Pro Met Ala Met Ala
    50                  55                  60
```

```
Pro Pro Pro Met Pro Met Thr Pro Pro Pro Met Pro Met Ala Pro Met
 65                  70                  75                  80

Pro Met Thr Pro Ser Ser Ser Pro Met Ser Pro Thr Thr Met Ala
             85                  90                  95

Pro Ser Pro Glu Thr Val Pro Asp Met Ala Ser Pro Met Met Pro
            100                 105                 110

Gly Met Glu Ser Ser Pro Ser Pro Gly Pro Met Pro Pro Ala Met Ala
            115                 120                 125

Ser Pro Asp Ser Gly Ala Phe Asn Val Arg Asn Asp Val Val Ala Ile
        130                 135                 140

Ser Phe Leu Val Ala Ala His Leu Leu Leu Val
145                 150                 155
```

<210> SEQ ID NO 4
<211> LENGTH: 152
<212> TYPE: PRT
<213> ORGANISM: Brassica napus
<220> FEATURE:
<221> NAME/KEY: misc_feature
<222> LOCATION: (1)..(152)
<223> OTHER INFORMATION: Public GI no. 62526422

<400> SEQUENCE: 4

```
Met Ala Leu Ser His Pro Met Thr Ile Phe Ser Leu Phe Leu Thr Phe
 1                   5                  10                  15

Leu Ala Leu Thr Ala Ala Gln Ser Pro Met Met Ala Pro Thr Met Pro
             20                  25                  30

Pro Ser Thr Met Ser Met Pro Pro Thr Thr Ser Thr Thr Thr Pro Pro
             35                  40                  45

Pro Met Ser Ser Met Ser Pro Pro Ser Ala Met Ser Pro Thr Pro
 50                  55                  60

Ser Thr Met Ser Pro Pro Pro Met Ser Pro Met Thr Pro Ser Met Ser
 65                  70                  75                  80

Pro Met Gly Pro Met Thr Pro Thr Met Ser Pro Met Asp Ser Pro Pro
             85                  90                  95

Ala Pro Ala Gly Pro Gly Met Ala Pro Gly Met Ser Thr Pro Gly Pro
            100                 105                 110

Ala Pro Gly Pro Met Gly Gly Glu Ser Met Ala Ser Pro Pro Pro Ser
            115                 120                 125

Ser Gly Phe Val His Gly Ile Ser Ile Ser Met Ala Met Val Ala Ile
        130                 135                 140

Ile Gly Ser Val Ala Leu Phe Phe
145                 150
```

<210> SEQ ID NO 5
<211> LENGTH: 150
<212> TYPE: PRT
<213> ORGANISM: Parthenium argentatum
<220> FEATURE:
<221> NAME/KEY: misc_feature
<222> LOCATION: (1)..(150)
<223> OTHER INFORMATION: Ceres CLONE ID no. 1606506

<400> SEQUENCE: 5

```
Met Ala Val Ser Arg Tyr Ile Ile Leu Leu Leu Ser Phe Thr Tyr Leu
 1                   5                  10                  15

Ala Ala Phe Ser Thr Ala Gln Ala Pro Ser Met Ser Pro Met Met Met
             20                  25                  30

Pro Met Ala Pro Pro Pro Ser Thr Met Pro Met Thr Pro Pro Pro Ser
```

```
            35                  40                  45
Thr Met Pro Met Thr Pro Pro Thr Pro Met Thr Met Thr Pro Pro
            50                  55                  60

Pro Met Met Met Pro Met Thr Pro Pro Pro Met Pro Met Gly Thr Pro
 65                  70                  75                  80

Pro Met Thr Met Pro Met Gly Pro Pro Met Met Met Pro Met Ser
                 85                  90                  95

Pro Gly Pro Ser Met Met Pro Ala Ser Pro Pro Ser Pro Met Gly Pro
            100                 105                 110

Ser Met Ala Pro Glu Pro Ala Thr Met Ser Pro Gly Pro Ser Met Thr
            115                 120                 125

Pro Ala Glu Thr Pro Ala Ser Gly Ala Ile Met Gln Tyr Ser Ser Ile
            130                 135                 140

Thr Met Leu Gly Ile Val
145                 150

<210> SEQ ID NO 6
<211> LENGTH: 586
<212> TYPE: DNA
<213> ORGANISM: Arabidopsis thaliana
<220> FEATURE:
<221> NAME/KEY: misc_feature
<222> LOCATION: (1)..(586)
<223> OTHER INFORMATION: Truncated Version of Ceres CLONE ID no. 30469
<220> FEATURE:
<221> NAME/KEY: CDS
<222> LOCATION: (59)..(293)
<223> OTHER INFORMATION: Referenced by SEQ ID NO: 7

<400> SEQUENCE: 6
aaaagatcta caaaacagag agttgtatac tttaaatcat ttagaggttg tgaaatatta      60
tggagagtga aggaaagatt gtgttcacag aagagcaaga ggctcttgta gtgaagtctt     120
ggagtgtcat gaagaaaaac tcagctgaat taggtctcaa actcttcatc aagatctttg     180
agattgcacc aacaacgaag aagatgttct ctttcttgag agactcacca attcctgctg     240
agcaaaatcc aaagctcaag cctcacgcaa tgtctgtttt tgtcatgtac aactgaggaa     300
aacagggaaa gttacggtga gggagactac tttgaagaga cttggagcca gccattctaa     360
atacggtgtc gttgacgaac actttgaggt ggccaagtat gcattgttgg agacgataaa     420
ggaggcagtg ccggagatgt ggtcaccgga gatgaaggtg gcttggggtc aggcttatga     480
tcaccttgtt gctgccatta agctgaaat gaatctttcc aactaaaaaa tcatatacta     540
ttatatagtt gtaaacttgt aataaatatt tcattttgaa ttgttc                    586

<210> SEQ ID NO 7
<211> LENGTH: 78
<212> TYPE: PRT
<213> ORGANISM: Arabidopsis thaliana

<400> SEQUENCE: 7

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60
```

```
Lys Leu Lys Pro His Ala Met Ser Val Phe Val Met Tyr Asn
 65                  70                  75
```

```
<210> SEQ ID NO 8
<211> LENGTH: 483
<212> TYPE: DNA
<213> ORGANISM: Arabidopsis thaliana
<220> FEATURE:
<221> NAME/KEY: misc_feature
<222> LOCATION: (1)..(483)
<223> OTHER INFORMATION: Full Version of Ceres CLONE ID no. 30469
<220> FEATURE:
<221> NAME/KEY: CDS
<222> LOCATION: (1)..(480)
<223> OTHER INFORMATION: Referenced by SEQ ID NO: 9

<400> SEQUENCE: 8
atggagagtg aaggaaagat tgtgttcaca gaagagcaag aggctcttgt agtgaagtct     60
tggagtgtca tgaagaaaaa ctcagctgaa ttaggtctca aactcttcat caagatcttt    120
gagattgcac caacaacgaa gaagatgttc tctttcttga gagactcacc aattcctgct    180
gagcaaaatc caaagctcaa gcctcacgca atgtctgttt ttgtcatgtg ttgtgaatca    240
gcagtacaac tgaggaaaac agggaaagtt acggtgaggg agactacttt gaagagactt    300
ggagccagcc attctaaata cggtgtcgtt gacgaacact ttgaggtggc caagtatgca    360
ttgttggaga cgataaagga ggcagtgccg gagatgtggt caccggagat gaaggtggct    420
tggggtcagg cttatgatca ccttgttgct gccattaaag ctgaaatgaa tctttccaac    480
taa    483
```

```
<210> SEQ ID NO 9
<211> LENGTH: 160
<212> TYPE: PRT
<213> ORGANISM: Arabidopsis thaliana

<400> SEQUENCE: 9

Met Glu Ser Glu Gly Lys Ile Val Phe Thr Glu Glu Gln Glu Ala Leu
 1               5                  10                  15

Val Val Lys Ser Trp Ser Val Met Lys Lys Asn Ser Ala Glu Leu Gly
             20                  25                  30

Leu Lys Leu Phe Ile Lys Ile Phe Glu Ile Ala Pro Thr Thr Lys Lys
         35                  40                  45

Met Phe Ser Phe Leu Arg Asp Ser Pro Ile Pro Ala Glu Gln Asn Pro
     50                  55                  60

Lys Leu Lys Pro His Ala Met Ser Val Phe Val Met Cys Cys Glu Ser
 65                  70                  75                  80

Ala Val Gln Leu Arg Lys Thr Gly Lys Val Thr Val Arg Glu Thr Thr
                 85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn
145                 150                 155                 160
```

```
<210> SEQ ID NO 10
<211> LENGTH: 160
<212> TYPE: PRT
```

```
<213> ORGANISM: Arabidopsis thaliana
<220> FEATURE:
<221> NAME/KEY: misc_feature
<222> LOCATION: (1)..(160)
<223> OTHER INFORMATION: Public GI no. 30909306

<400> SEQUENCE: 10

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
                20                  25                  30

Leu Lys Leu Phe Ile Lys Ile Phe Glu Ile Ala Pro Thr Ala Lys Lys
            35                  40                  45

Leu Phe Ser Phe Leu Arg Asp Ser Pro Ile Pro Ala Glu Gln Asn Pro
50                  55                  60

Lys Leu Lys Pro His Ala Met Ser Val Phe Val Met Cys Cys Glu Ser
65                  70                  75                  80

Ala Ala Gln Leu Arg Lys Thr Gly Lys Val Thr Val Lys Glu Thr Thr
                85                  90                  95

Leu Lys Arg Leu Gly Ala Asn His Ser Lys Tyr Gly Val Val Asp Glu
            100                 105                 110

His Phe Glu Val Thr Lys Tyr Ala Leu Leu Glu Thr Ile Lys Glu Ala
        115                 120                 125

Val Pro Glu Met Trp Ser Pro Glu Met Lys Ser Ala Trp Gly Gln Ala
130                 135                 140

Tyr Asp His Leu Val Ala Ala Ile Lys Ala Glu Met Lys Pro Ser His
145                 150                 155                 160

<210> SEQ ID NO 11
<211> LENGTH: 158
<212> TYPE: PRT
<213> ORGANISM: Arabidopsis thaliana
<220> FEATURE:
<221> NAME/KEY: misc_feature
<222> LOCATION: (1)..(158)
<223> OTHER INFORMATION: Public GI no. 37903656

<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
                20                  25                  30

Phe Leu Lys Ile Phe Glu Ile Ala Pro Ser Ala Gln Lys Leu Phe Ser
            35                  40                  45

Phe Leu Arg Asp Ser Asp Ile Pro Leu Glu Lys Asn Pro Lys Leu Lys
50                  55                  60

Pro His Ala Met Ser Val Phe Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
            100                 105                 110

Val Thr Lys Phe Ala Leu Leu Glu Thr Ile Lys Glu Ala Leu Pro Glu
        115                 120                 125

Met Trp Ser Pro Glu Met Lys Asn Ala Trp Gly Glu Ala Tyr Asp Gln
130                 135                 140

Leu Val Ala Ala Ile Lys Ser Glu Met Lys Pro Pro Leu Asn
145                 150                 155
```

<210> SEQ ID NO 12
<211> LENGTH: 163
<212> TYPE: PRT
<213> ORGANISM: Arabidopsis thaliana
<220> FEATURE:
<221> NAME/KEY: misc_feature
<222> LOCATION: (1)..(163)
<223> OTHER INFORMATION: Public GI no. 15824736

<400> SEQUENCE: 12

```
Met Ala Thr Tyr Glu Gly Lys Val Phe Thr Glu Glu Gln Glu Ala Leu
1               5                   10                  15

Val Val Lys Ser Trp Thr Val Met Lys Lys Thr Ala Glu Leu Gly
            20                  25                  30

Leu Lys Phe Phe Leu Lys Ile Phe Glu Ile Ala Pro Ser Ala Lys Lys
            35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
                100                 105                 110

His Phe Glu Val Thr Lys Phe Ala Leu Leu Glu Thr Ile Lys Glu Ala
            115                 120                 125

Val Pro Asp Met Trp Ser Asp Glu Met Lys Asn Ala Trp Gly Glu Ala
        130                 135                 140

Tyr Asp Arg Leu Val Ala Ala Ile Lys Ile Glu Met Lys Ala Cys Ser
145                 150                 155                 160

Gln Ala Ala
```

<210> SEQ ID NO 13
<211> LENGTH: 161
<212> TYPE: PRT
<213> ORGANISM: Glycine max
<220> FEATURE:
<221> NAME/KEY: misc_feature
<222> LOCATION: (1)..(161)
<223> OTHER INFORMATION: Ceres CLONE ID no. 546001

<400> SEQUENCE: 13

```
Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
            35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met Thr Cys Asp Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
                100                 105                 110

His Phe Glu Val Thr Lys Phe Ala Leu Leu Glu Thr Ile Lys Glu Ala
```

-continued

```
            115                 120                 125
Val Pro Glu Met Trp Ser Pro Ala Met Lys Asn Ala Trp Gly Glu Ala
    130                 135                 140

Tyr Asp Gln Leu Val Asp Ala Ile Lys Ser Glu Met Lys Pro Pro Ser
145                 150                 155                 160

Ser

<210> SEQ ID NO 14
<211> LENGTH: 160
<212> TYPE: PRT
<213> ORGANISM: Glycine max
<220> FEATURE:
<221> NAME/KEY: misc_feature
<222> LOCATION: (1)..(160)
<223> OTHER INFORMATION: Public GI no. 11095158

<400> SEQUENCE: 14

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
                20                  25                  30

Leu Lys Leu Phe Leu Lys Ile Phe Glu Ile Ala Pro Ser Ala Gln Lys
            35                  40                  45

Leu Phe Ser Phe Leu Lys Asp Ser Lys Val Pro Leu Glu Gln Asn Thr
        50                  55                  60

Lys Leu Lys Pro His Ala Met Ser Val Phe Leu Met Thr Cys Glu Ser
65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asn Ala Ile Lys Ser Glu Met Lys Pro Ser Ser
145                 150                 155                 160

<210> SEQ ID NO 15
<211> LENGTH: 152
<212> TYPE: PRT
<213> ORGANISM: Glycine max
<220> FEATURE:
<221> NAME/KEY: misc_feature
<222> LOCATION: (1)..(152)
<223> OTHER INFORMATION: Public GI no. 12963875

<400> SEQUENCE: 15

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
                20                  25                  30

Lys Ile Phe Glu Ile Ala Pro Ser Ala Lys Lys Met Phe Ser Phe Leu
            35                  40                  45

Lys Asp Ser Asn Val Pro Leu Asp Gln Asn Pro Lys Leu Lys Ile His
        50                  55                  60

Ala Lys Ser Val Leu Val Met Thr Cys Glu Ala Ala Val Gln Leu Arg
65                  70                  75                  80
```

```
Lys Ala Gly Lys Val Val Arg Asp Ser Thr Leu Lys Lys Ile Gly
                85                  90                  95

Ala Thr His Phe Lys Tyr Gly Val Val Asp Glu His Phe Glu Val Thr
            100                 105                 110

Lys Tyr Ala Leu Leu Glu Thr Ile Lys Glu Ala Ser Gln Glu Met Trp
        115                 120                 125

Ser Val Glu Met Lys Asn Ala Trp Gly Glu Ala Tyr Asp Gln Leu Val
130                 135                 140

Ser Ala Ile Lys Thr Glu Met Lys
145                 150

<210> SEQ ID NO 16
<211> LENGTH: 165
<212> TYPE: PRT
<213> ORGANISM: Zea mays
<220> FEATURE:
<221> NAME/KEY: misc_feature
<222> LOCATION: (1)..(165)
<223> OTHER INFORMATION: Ceres CLONE ID no. 1554560

<400> SEQUENCE: 16

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
145                 150                 155                 160

Met Lys Pro Asp Ala
                165

<210> SEQ ID NO 17
<211> LENGTH: 162
<212> TYPE: PRT
<213> ORGANISM: Triticum aestivum
<220> FEATURE:
<221> NAME/KEY: misc_feature
<222> LOCATION: (1)..(162)
<223> OTHER INFORMATION: Ceres CLONE ID no. 839727

<400> SEQUENCE: 17

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
```

```
                35                  40                  45
Gln Met Phe Pro Phe Leu Arg Asp Ser Asp Val Pro Leu Glu Thr Asn
         50                  55                  60

Pro Lys Leu Lys Thr His Ala Val Ser Val Phe Val Met Thr Cys Glu
 65                  70                  75                  80

Ala Ala Ala Gln Leu Arg Lys Ala Gly Lys Ile Thr Val Arg Glu Thr
                 85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145                 150                 155                 160

Ser Glu

<210> SEQ ID NO 18
<211> LENGTH: 169
<212> TYPE: PRT
<213> ORGANISM: Triticum aestivum
<220> FEATURE:
<221> NAME/KEY: misc_feature
<222> LOCATION: (1)..(169)
<223> OTHER INFORMATION: Public GI no. 14701800

<400> SEQUENCE: 18

Met Ala Leu Val Glu Gly Asn Asn Gly Val Ser Gly Gly Ala Val Ser
 1               5                  10                  15

Phe Ser Glu Glu Gln Glu Ala Leu Val Leu Lys Ser Trp Ala Ile Met
                 20                  25                  30

Lys Lys Asp Ser Ala Asn Ile Gly Leu Arg Phe Phe Leu Lys Ile Phe
            35                  40                  45

Glu Val Ala Pro Ser Ala Ser Gln Met Phe Ser Phe Leu Arg Asn Ser
 50                  55                  60

Asp Val Pro Leu Glu Lys Asn Pro Lys Leu Lys Thr His Ala Met Ser
 65                  70                  75                  80

Val Phe Val Met Thr Cys Glu Ala Ala Ala Gln Leu Arg Lys Ala Gly
                 85                  90                  95

Lys Val Thr Val Arg Asp Thr Thr Leu Lys Arg Leu Gly Ala Thr His
            100                 105                 110

Phe Lys Tyr Gly Val Gly Asp Ala His Phe Glu Val Thr Arg Phe Ala
        115                 120                 125

Leu Leu Glu Thr Ile Lys Glu Ala Val Pro Val Asp Met Trp Ser Pro
    130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165

<210> SEQ ID NO 19
<211> LENGTH: 416
<212> TYPE: DNA
<213> ORGANISM: Arabidopsis thaliana
<220> FEATURE:
<221> NAME/KEY: misc_feature
<222> LOCATION: (1)..(416)
<223> OTHER INFORMATION: Ceres CLONE ID no. 271922
```

```
<220> FEATURE:
<221> NAME/KEY: CDS
<222> LOCATION: (57)..(333)
<223> OTHER INFORMATION: Referenced by SEQ ID NO: 20

<400> SEQUENCE: 19
gctcattagg gtttctcatc tacgacggcg tggtgttcct ccttcctgct ctgaaaaatg     60
gcgaagagaa cgaagaaggt tggaatcgtc ggcaaatacg gaacacgtta tggtgcgagt    120
atcaggaagc agattaagaa gatggaggtc agccagcaca gcaagtactt ctgtgagttc    180
tgtggcaagt acggagtgaa gcgaaaggct gttggtatct ggggttgcaa ggattgtggc    240
aaggtcaagg caggtggtgc ttacacaatg aacaccgcca gtgcggtcac tgttagaagc    300
acgatcagaa ggttgaggga gcagatcgag ggttaaaagt ctgctggctt tttatatttg    360
gtttccttgt tttgacaatt taagttttgc atcaacagtg agaacatgtt ttgatt        416

<210> SEQ ID NO 20
<211> LENGTH: 92
<212> TYPE: PRT
<213> ORGANISM: Arabidopsis thaliana
<220> FEATURE:
<221> NAME/KEY: misc_feature
<222> LOCATION: (2)..(91)
<223> OTHER INFORMATION: Pfam Name: Ribosomal_L37ae; Pfam Description:
      Ribosomal L37ae protein family

<400> SEQUENCE: 20

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
            20                  25                  30

Gln His Ser Lys Tyr Phe Cys Glu Phe Cys Gly Lys Tyr Gly Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 21
<211> LENGTH: 92
<212> TYPE: PRT
<213> ORGANISM: Arabidopsis thaliana
<220> FEATURE:
<221> NAME/KEY: misc_feature
<222> LOCATION: (1)..(92)
<223> OTHER INFORMATION: Public GI no. 4090257

<400> SEQUENCE: 21

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Pro Ser Ala Val Thr Val Arg
65                  70                  75                  80
```

-continued

Ser Thr Ile Arg Arg Leu Arg Glu Gln Thr Glu Gly
                85                  90

<210> SEQ ID NO 22
<211> LENGTH: 92
<212> TYPE: PRT
<213> ORGANISM: Arabidopsis thaliana
<220> FEATURE:
<221> NAME/KEY: misc_feature
<222> LOCATION: (1)..(92)
<223> OTHER INFORMATION: Public GI no. 4741896

<400> SEQUENCE: 22

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Tyr Ala Val Lys
            35                  40                  45

Arg Lys Ala Val Gly Ile Trp Gly Cys Lys Ala Cys Gly Lys Val Lys
        50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 23
<211> LENGTH: 92
<212> TYPE: PRT
<213> ORGANISM: Arabidopsis thaliana
<220> FEATURE:
<221> NAME/KEY: misc_feature
<222> LOCATION: (1)..(92)
<223> OTHER INFORMATION: Ceres CLONE ID no. 36046
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other

<400> SEQUENCE: 23

Met Ala Lys Arg Thr Lys Lys Val Gly Ile Val Gly Lys Tyr Gly Thr
1               5                   10                  15

Arg Tyr Gly Ala Ser Ile Arg Lys Gln Ile Lys Lys Met Glu Val Ser
                20                  25                  30

Gln His Ser Lys Tyr Phe Cys Glu Phe Cys Gly Lys Xaa Gly Val Lys
            35                  40                  45

Xaa Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Ile Glu Gly
                85                  90

<210> SEQ ID NO 24
<211> LENGTH: 92
<212> TYPE: PRT
<213> ORGANISM: Arabidopsis thaliana
<220> FEATURE:
<221> NAME/KEY: misc_feature
<222> LOCATION: (1)..(92)

-continued

<223> OTHER INFORMATION: Public GI no. 6016699

<400> SEQUENCE: 24

Met Thr Lys Arg Thr Lys Lys Ala Arg Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Asn Lys Tyr Phe Cys Glu Phe Cys Gly Lys Tyr Ser Val Lys
        35                  40                  45

Arg Lys Val Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ser
            85                  90

<210> SEQ ID NO 25
<211> LENGTH: 92
<212> TYPE: PRT
<213> ORGANISM: Glycine max
<220> FEATURE:
<221> NAME/KEY: misc_feature
<222> LOCATION: (1)..(92)
<223> OTHER INFORMATION: Ceres CLONE ID no. 664936

<400> SEQUENCE: 25

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Gly
            85                  90

<210> SEQ ID NO 26
<211> LENGTH: 92
<212> TYPE: PRT
<213> ORGANISM: Glycine max
<220> FEATURE:
<221> NAME/KEY: misc_feature
<222> LOCATION: (1)..(92)
<223> OTHER INFORMATION: Ceres CLONE ID no. 658438

<400> SEQUENCE: 26

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
            85                  90

<210> SEQ ID NO 27
<211> LENGTH: 92
<212> TYPE: PRT
<213> ORGANISM: Glycine max
<220> FEATURE:
<221> NAME/KEY: misc_feature
<222> LOCATION: (1)..(92)
<223> OTHER INFORMATION: Ceres CLONE ID no. 1049262

<400> SEQUENCE: 27

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Phe Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
            85                  90

<210> SEQ ID NO 28
<211> LENGTH: 92
<212> TYPE: PRT
<213> ORGANISM: Triticum aestivum
<220> FEATURE:
<221> NAME/KEY: misc_feature
<222> LOCATION: (1)..(92)
<223> OTHER INFORMATION: Ceres CLONE ID no. 632613

<400> SEQUENCE: 28

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
            85                  90

<210> SEQ ID NO 29
<211> LENGTH: 92
<212> TYPE: PRT
<213> ORGANISM: Zea mays
<220> FEATURE:
<221> NAME/KEY: misc_feature
<222> LOCATION: (1)..(92)
<223> OTHER INFORMATION: Ceres CLONE ID no. 1390976

<400> SEQUENCE: 29

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser

```
                    20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 30
<211> LENGTH: 92
<212> TYPE: PRT
<213> ORGANISM: Zea mays
<220> FEATURE:
<221> NAME/KEY: misc_feature
<222> LOCATION: (1)..(92)
<223> OTHER INFORMATION: Ceres CLONE ID no. 1457185

<400> SEQUENCE: 30

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 31
<211> LENGTH: 92
<212> TYPE: PRT
<213> ORGANISM: Zea mays
<220> FEATURE:
<221> NAME/KEY: misc_feature
<222> LOCATION: (1)..(92)
<223> OTHER INFORMATION: Public GI no. 56202147

<400> SEQUENCE: 31

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 32
<211> LENGTH: 92
<212> TYPE: PRT
<213> ORGANISM: Zea mays
```

```
<220> FEATURE:
<221> NAME/KEY: misc_feature
<222> LOCATION: (1)..(92)
<223> OTHER INFORMATION: Public GI no. 58578274

<400> SEQUENCE: 32

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Glu Tyr Phe Cys Glu Phe Cys Gly Lys Tyr Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

<210> SEQ ID NO 33
<211> LENGTH: 632
<212> TYPE: DNA
<213> ORGANISM: Arabidopsis thaliana
<220> FEATURE:
<221> NAME/KEY: misc_feature
<222> LOCATION: (1)..(632)
<223> OTHER INFORMATION: Ceres CLONE ID no. 2403
<220> FEATURE:
<221> NAME/KEY: CDS
<222> LOCATION: (50)..(512)
<223> OTHER INFORMATION: Referenced by SEQ ID NO: 34

<400> SEQUENCE: 33
attccccatc gcacagaccc gcctaagaat ccgagagaga agaagagata atgcagatct      60
tcgtcaaaac cctcaccggc aaaactataa ccctagaggt tgagagcagc gacaccatcg     120
acaatgttaa agccaaaatc caggacaaat agggcatacc acctgatcaa cagaggctga     180
tttttgctgg taagcaattg gaagatggcc ggaccttagc tgactacaac atccagaaag     240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcatc tatgccggaa     420
aacagcttgc tgatgacaaa acggccaaag attatgcgat agagggaggc tctgttcttc     480
atttggttct tgctcttagg ggtggtcttc tctgatctga ataaataagc ttttcaacaa     540
acatctttcc cctcactatt gtcctccttt tgtggaattc atgacacaca aaaattgcta     600
tgggaaattg gaatattatg atgttttttc tc                                   632

<210> SEQ ID NO 34
<211> LENGTH: 154
<212> TYPE: PRT
<213> ORGANISM: Arabidopsis thaliana
<220> FEATURE:
<221> NAME/KEY: misc_feature
<222> LOCATION: (77)..(150)
<223> OTHER INFORMATION: Pfam Name: ubiquitin; Pfam Description:
      Ubiquitin family

<400> SEQUENCE: 34

Met Gln Ile Phe Val Lys Thr Leu Thr Gly Lys Thr Ile Thr Leu Glu
1               5                   10                  15
```

-continued

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Lys Glu Gly Ile
            100                 105                 110

Pro Pro Val Gln Gln Arg Leu Ile Tyr Ala Gly Lys Gln Leu Ala Asp
            115                 120                 125

Asp Lys Thr Ala Lys Asp Tyr Ala Ile Glu Gly Ser Val Leu His
        130                 135                 140

Leu Val Leu Ala Leu Arg Gly Gly Leu Leu
145                 150

<210> SEQ ID NO 35
<211> LENGTH: 169
<212> TYPE: PRT
<213> ORGANISM: Zea mays
<220> FEATURE:
<221> NAME/KEY: misc_feature
<222> LOCATION: (1)..(169)
<223> OTHER INFORMATION: Ceres CLONE ID no. 1482731

<400> SEQUENCE: 35

Lys Asn Ser Leu Ile Glu Lys Lys Lys Glu Arg Lys Glu Lys Met
1               5                   10                  15

Gln Ile Phe Val Lys Thr Leu Thr Gly Lys Thr Ile Thr Leu Glu Val
            20                  25                  30

Glu Ser Ser Asp Thr Ile Asp Asn Val Lys Ser Lys Ile Gln Asp Lys
        35                  40                  45

Glu Gly Ile Pro Pro Asp Gln Gln Arg Leu Ile Phe Ala Gly Lys Gln
    50                  55                  60

Leu Glu Asp Gly Arg Thr Leu Ala Asp Tyr Asn Ile Gln Lys Glu Ser
65                  70                  75                  80

Thr Leu His Leu Val Leu Arg Leu Arg Gly Gly Thr Met Ile Lys Val
                85                  90                  95

Lys Thr Leu Thr Gly Lys Glu Ile Glu Ile Asp Ile Glu Pro Thr Asp
            100                 105                 110

Thr Ile Asp Arg Ile Lys Glu Arg Val Glu Glu Lys Glu Gly Ile Pro
        115                 120                 125

Pro Val Gln Gln Arg Leu Ile Tyr Ala Gly Lys Gln Leu Ala Asp Asp
    130                 135                 140

Lys Thr Ala Lys Asp Tyr Asn Ile Glu Gly Gly Ser Val Leu His Leu
145                 150                 155                 160

Val Leu Ala Leu Arg Gly Gly Ser Asp
                165

<210> SEQ ID NO 36
<211> LENGTH: 154
<212> TYPE: PRT
<213> ORGANISM: Glycine max
<220> FEATURE:
<221> NAME/KEY: misc_feature

```
<222> LOCATION: (1)..(154)
<223> OTHER INFORMATION: Ceres CLONE ID no. 522921

<400> SEQUENCE: 36

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Glu Tyr Asn Ile Glu Gly Gly Ser Val Leu His
130                 135                 140

Leu Val Leu Ala Leu Arg Gly Gly Thr Tyr
145                 150

<210> SEQ ID NO 37
<211> LENGTH: 160
<212> TYPE: PRT
<213> ORGANISM: Brassica napus
<220> FEATURE:
<221> NAME/KEY: misc_feature
<222> LOCATION: (1)..(160)
<223> OTHER INFORMATION: Ceres CLONE ID no. 1036726
<220> FEATURE:
<221> NAME/KEY: misc_feature
<222> LOCATION: (145)..(145)
<223> OTHER INFORMATION: Xaa is any aa, unknown, or other

<400> SEQUENCE: 37

Asn Gln Ile Lys Lys Ser Leu Ser Lys Lys Arg Lys Lys Met Gln Ile
1               5                   10                  15

Phe Val Lys Thr Leu Thr Gly Lys Thr Ile Thr Leu Glu Val Glu Ser
            20                  25                  30

Ser Asp Thr Ile Asp Asn Val Lys Ala Lys Ile Gln Asp Lys Glu Gly
        35                  40                  45

Ile Pro Pro Asp Gln Gln Arg Leu Ile Phe Ala Gly Lys Gln Leu Glu
    50                  55                  60

Asp Gly Arg Thr Leu Ala Asp Tyr Asn Ile Gln Lys Glu Ser Thr Leu
65                  70                  75                  80

His Leu Val Leu Arg Leu Arg Gly Gly Thr Met Ile Lys Val Lys Thr
                85                  90                  95

Leu Thr Gly Lys Glu Ile Glu Ile Asp Ile Glu Pro Thr Asp Thr Ile
            100                 105                 110

Asp Arg Ile Lys Glu Arg Val Glu Glu Lys Glu Gly Ile Pro Pro Val
        115                 120                 125

Gln Gln Arg Leu Ile Tyr Ala Gly Lys Gln Leu Ala Asp Asp Lys Thr
130                 135                 140

Xaa Lys Asp Tyr Asn Ile Glu Gly Gly Ser Val Ser Ala Ser Gly Ser
```

-continued

```
145                 150                 155                 160

<210> SEQ ID NO 38
<211> LENGTH: 188
<212> TYPE: PRT
<213> ORGANISM: Glycine max
<220> FEATURE:
<221> NAME/KEY: misc_feature
<222> LOCATION: (1)..(188)
<223> OTHER INFORMATION: Ceres CLONE ID no. 513071
<220> FEATURE:
<221> NAME/KEY: misc_feature
<222> LOCATION: (181)..(181)
<223> OTHER INFORMATION: Xaa is any aa, unknown, or other

<400> SEQUENCE: 38

Lys Lys Lys Glu Ile Phe Leu Gly Val Leu Arg Leu Arg Cys His Lys
1               5                   10                  15

Val Arg Val Arg His Arg Leu Val Arg Leu Cys Glu Gly Gly Arg Gly
            20                  25                  30

Glu Glu Lys Met Gln Ile Phe Val Lys Thr Leu Thr Gly Lys Thr Ile
        35                  40                  45

Thr Leu Glu Val Glu Ser Ser Asp Thr Val Asp Asn Val Lys Ala Lys
    50                  55                  60

Ile Gln Asp Lys Glu Gly Ile Pro Pro Asp Gln Gln Arg Leu Ile Phe
65                  70                  75                  80

Ala Gly Lys Gln Leu Glu Asp Gly Arg Thr Leu Ala Asp Tyr Asn Ile
                85                  90                  95

Gln Lys Glu Ser Thr Leu His Leu Val Leu Arg Leu Arg Gly Gly Thr
            100                 105                 110

Met Ile Lys Val Lys Thr Leu Thr Gly Lys Glu Ile Glu Ile Asp Ile
        115                 120                 125

Glu Pro Thr Asp Ser Ile Asp Arg Ile Lys Glu Arg Val Glu Glu Lys
    130                 135                 140

Glu Gly Ile Pro Pro Val Gln Gln Arg Leu Ile Tyr Ala Gly Lys Gln
145                 150                 155                 160

Leu Ala Asp Asp Lys Thr Ala Lys Asp Tyr Asn Ile Glu Gly Gly Ser
                165                 170                 175

Val Leu His Leu Xaa Leu Ala Leu Arg Gly Gly Tyr
            180                 185

<210> SEQ ID NO 39
<211> LENGTH: 620
<212> TYPE: DNA
<213> ORGANISM: Arabidopsis thaliana
<220> FEATURE:
<221> NAME/KEY: misc_feature
<222> LOCATION: (1)..(620)
<223> OTHER INFORMATION: Ceres CLONE ID no. 2403
<220> FEATURE:
<221> NAME/KEY: CDS
<222> LOCATION: (50)..(149)
<223> OTHER INFORMATION: Referenced by SEQ ID NO: 40

<400> SEQUENCE: 39
attccccatc gcacagaccc ccctaagaat ccgagagaga agaagagata atgcagatct     60
tcgtcaaaac cctcaccggc aaaactataa ccctagaagt tgagagcagc gacaccatcg    120
acaatgttaa agccaaaatc caggacaaag agggcatacc acctgatcaa cagaggctga    180
tttttgctgg taagcaattg gaagatggcc ggaccttagc tgattacaac atccagaaag    240
agtctactct tcatcttgtc ctcaggctca gaggtggaac catgatcaag gtgaagacac    300
```

-continued

```
tcactggaaa agaaatcgag attgatatcg aaccaaccga cactattgat cggatcaaag    360
aacgtgttga agagaaagaa ggcatccctc ctgttcaaca aaggctcata tatgccggaa    420
aacagcttgc tgatgacaaa acggccaaag attatgcgat agagggaggc tctgttcttc    480
atttggttct tgctcttagg ggtggtcttc tctgatctta ataaataagc ttttcaacaa    540
acatcttttc cctcactatt gtcctcctta tgtggaattc atgacacacc aaaattgcta    600
tgggaaattg gaatattatg                                                620
```

<210> SEQ ID NO 40
<211> LENGTH: 33
<212> TYPE: PRT
<213> ORGANISM: Arabidopsis thaliana
<220> FEATURE:
<221> NAME/KEY: misc_feature
<222> LOCATION: (77)..(150)
<223> OTHER INFORMATION: Pfam Name: ubiquitin; Pfam Description:
    Ubiquitin family

<400> SEQUENCE: 40

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys
```

<210> SEQ ID NO 41
<211> LENGTH: 1106
<212> TYPE: DNA
<213> ORGANISM: Glycine max
<220> FEATURE:
<221> NAME/KEY: misc_feature
<222> LOCATION: (1)..(1106)
<223> OTHER INFORMATION: Ceres CLONE ID no. 674166
<220> FEATURE:
<221> NAME/KEY: CDS
<222> LOCATION: (397)..(1027)
<223> OTHER INFORMATION: Referenced by SEQ ID NO: 42

<400> SEQUENCE: 41

```
atatttttgt gtagatgaag atcaacaaga gaaggtgttg ttgtgagttg tgttgttatg    60
gtaccttcct tcaaccacaa aacctctctc cctctaccac ccattctctt ctctctctct   120
ctctcccgtc ctccatctct caccttctca atctcttcac caccaccatc atcatcatta   180
tcttctccaa tctctataac ctcgaaatcc ctcaaaacct ctccctcaaa ccaaatgaaa   240 tgacccttttt gtgagaacat tttttccccc ttaagaaaag gtcaaaggct gcaacttttt   300
cttaaccaat ctcacatttt tttattttc aacgtatttt ggccaggttt ggttttctgg    360
gttgtcttgg aattcaaaaa agattccaac tttgaagatg gtaggggtg gaaccgccgc    420 ggcggcggcg gaggtcgccg aacccggttt aaggccggtt tatttcaaag aacagcgata   480 tagggggcgtc agaaaaagac cgtggggccg gttcgctgcc gaaatcagag acccttttgaa   540 gaaagccagg gtttggctcg gaacctttga caccgccgag gaggcggcgc gtgcctacga   600
cacggcggcg agaaccctcc ggggaccaaa ggcgaagacc aatttccctc tttctccgcc   660
gttctaccat cccgatccat tttccgatca ccggcacttc gccaacaccg gcgaagattt   720
ccacgatcac cggcgaccaa catccagtgg catgagcagc accgtagagt ccttcagcgg   780
cccccgtgct gccgtgccgg cgacagcgcc ggtggccacc ggccgagat atccccggac    840 gccacccgtt atccccgagg actgccgcag cgactgcgat tcgtcgtcct ccgtcgttga   900
```

```
cgacggcgaa ggcgacaacg tggcgtcgtc gttcccgcga gaaccgttgc cgtttgatct    960
aaacgcgttg ccgttagacg atgctgacgt ggcaaccgat gatctgttct gcaccgttct   1020
ttgcctctga tgagaaaaaa tgaaaaaacg gaacgaaatg atgtatttgg ttcgttgacg   1080
gaattattat tattttttc tttctt                                          1106
```

<210> SEQ ID NO 42
<211> LENGTH: 210
<212> TYPE: PRT
<213> ORGANISM: Glycine max
<220> FEATURE:
<221> NAME/KEY: misc_feature
<222> LOCATION: (26)..(89)
<223> OTHER INFORMATION: Pfam Name: AP2; Pfam Description: AP2 domain

<400> SEQUENCE: 42

```
Met Gly Arg Gly Gly Thr Ala Ala Ala Ala Glu Val Ala Glu Pro
1               5                   10                  15

Gly Leu Arg Pro Val Tyr Phe Lys Glu Gln Arg Tyr Arg Gly Val Arg
                20                  25                  30

Lys Arg Pro Trp Gly Arg Phe Ala Ala Glu Ile Arg Asp Pro Leu Lys
            35                  40                  45

Lys Ala Arg Val Trp Leu Gly Thr Phe Asp Thr Ala Glu Glu Ala Ala
        50                  55                  60

Arg Ala Tyr Asp Thr Ala Ala Arg Thr Leu Arg Gly Pro Lys Ala Lys
65                  70                  75                  80

Thr Asn Phe Pro Leu Ser Pro Pro Phe Tyr His Pro Asp Pro Phe Ser
                85                  90                  95

Asp His Arg His Phe Ala Asn Thr Gly Glu Asp Phe Asp His Arg
            100                 105                 110

Arg Pro Thr Ser Ser Gly Met Ser Ser Thr Val Glu Ser Phe Ser Gly
        115                 120                 125

Pro Arg Ala Ala Val Pro Ala Thr Ala Pro Val Ala Thr Gly Arg Arg
    130                 135                 140

Tyr Pro Arg Thr Pro Pro Val Ile Pro Glu Asp Cys Arg Ser Asp Cys
145                 150                 155                 160

Asp Ser Ser Ser Val Val Asp Asp Gly Glu Gly Asp Asn Val Ala
                165                 170                 175

Ser Ser Phe Pro Arg Glu Pro Leu Pro Phe Asp Leu Asn Ala Leu Pro
            180                 185                 190

Leu Asp Asp Ala Asp Val Ala Thr Asp Asp Leu Phe Cys Thr Val Leu
        195                 200                 205

Cys Leu
```

<210> SEQ ID NO 43
<211> LENGTH: 225
<212> TYPE: PRT
<213> ORGANISM: Glycine max
<220> FEATURE:
<221> NAME/KEY: misc_feature
<222> LOCATION: (1)..(225)
<223> OTHER INFORMATION: Public GI no. 12322345

<400> SEQUENCE: 43

```
Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
                20                  25                  30
```

-continued

```
Lys Arg Pro Trp Gly Arg Phe Ala Ala Glu Ile Arg Asp Pro Trp Lys
         35                  40                  45

Lys Ala Arg Val Trp Leu Gly Thr Phe Asp Ser Ala Glu Glu Ala Ala
 50                  55                  60

Arg Ala Tyr Asp Ser Ala Ala Arg Asn Leu Arg Gly Pro Lys Ala Lys
 65                  70                  75                  80

Thr Asn Phe Pro Ile Asp Ser Ser Pro Pro Pro Asn Leu Arg
                 85                  90                  95

Phe Asn Gln Ile Arg Asn Gln Asn Gln Val Asp Pro Phe Met
                100                 105                 110

Asp His Arg Leu Phe Thr Asp His Gln Gln Gln Phe Pro Ile Val Asn
                115                 120                 125

Arg Pro Thr Ser Ser Ser Met Ser Ser Thr Val Glu Ser Phe Ser Gly
    130                 135                 140

Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Arg Arg
                180                 185                 190

Arg Asn Pro Pro Phe Gln Phe Asp Leu Asn Phe Pro Pro Leu Asp Cys
    195                 200                 205

Val Asp Leu Phe Asn Gly Ala Asp Asp Leu His Cys Thr Asp Leu Arg
210                 215                 220

Leu
225

<210> SEQ ID NO 44
<211> LENGTH: 215
<212> TYPE: PRT
<213> ORGANISM: Brassica napus
<220> FEATURE:
<221> NAME/KEY: misc_feature
<222> LOCATION: (1)..(215)
<223> OTHER INFORMATION: Ceres CLONE ID no. 975672
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other

<400> SEQUENCE: 44

Met Arg Lys Gly Arg Gly Ser Ser Ala Val Pro Pro Ala Leu Pro Gly
 1               5                  10                  15

Ser Val Lys Glu Pro Arg Tyr Arg Gly Val Arg Lys Arg Pro Trp Gly
                 20                  25                  30

Arg Phe Ala Ala Glu Ile Arg Asp Pro Leu Lys Lys Ser Arg Val Trp
```

-continued

```
                35                  40                  45
Leu Gly Thr Phe Asp Ser Ala Glu Glu Ala Ala Arg Ala Tyr Asp Ala
 50                  55                  60

Ala Ala Arg Asn Leu Arg Gly Pro Lys Ala Lys Thr Asn Phe Gln Ile
 65                  70                  75                  80

Asp Cys Ser Pro Ser Pro Leu Gln Pro Leu His His Arg Asn Gln
                 85                  90                  95

Ile Asp Pro Phe Met Asp His Arg Leu Tyr Gly Gly Glu Gln Glu Val
                100                 105                 110

Val Ile Ile Ser Arg Pro Ala Ser Ser Met Ser Ser Thr Val Lys
                115                 120                 125

Ser Cys Ser Gly Val Arg Pro Ala Ser Ser Val Ala Lys Ala Ala
130                 135                 140

Thr Lys Arg Tyr Pro Arg Thr Pro Pro Val Ala Pro Glu Asp Cys Arg
145                 150                 155                 160

Ser Asp Cys Asp Ser Ser Ser Val Val Glu Asp Gly Xaa Asp Ile
                165                 170                 175

Ala Ser Ser Ser Arg Arg Lys Pro Pro Phe Glu Phe Asp Leu Asn
                180                 185                 190

Phe Xaa Pro Leu Asp Gly Val Asp Leu Phe Val Gly Ala Asp Asp Xaa
                195                 200                 205

Xaa Cys Thr Asp Leu Xaa Leu
210                 215
```

<210> SEQ ID NO 45
<211> LENGTH: 211
<212> TYPE: PRT
<213> ORGANISM: Zea mays
<220> FEATURE:
<221> NAME/KEY: misc_feature
<222> LOCATION: (1)..(211)
<223> OTHER INFORMATION: Ceres CLONE ID no. 273307

<400> SEQUENCE: 45

```
Met Arg Arg Arg Gly Val Ala Ala Asp Ala Asp Gly Asp Val Glu
 1               5                  10                  15

Leu Arg Phe Arg Gly Val Arg Lys Arg Pro Trp Gly Arg Tyr Ala Ala
                 20                  25                  30

Glu Ile Arg Asp Pro Ala Lys Lys Ala Arg Val Trp Leu Gly Thr Phe
                 35                  40                  45

Asp Ser Ala Glu Asp Ala Ala Arg Ala Tyr Asp Ala Ala Ala Arg Met
 50                  55                  60

Leu Arg Gly Pro Lys Ala Arg Thr Asn Phe Pro Leu Pro Ala Ala Ala
 65                  70                  75                  80

Ala Leu His His Pro His Met Pro Ala Ala Ala Ala Ala Pro
                 85                  90                  95

Pro Tyr Thr Thr Tyr Pro Thr Ala Thr Gly Val Val Ser Thr Pro Pro
                100                 105                 110

Val Ala Arg Pro Ala Cys Ser Ser Leu Ser Ser Thr Val Glu Ser Phe
                115                 120                 125

Ser Gly Ala Arg Pro Arg Pro Val Leu Pro Arg Phe Pro Pro Pro
130                 135                 140

Ser Ile Pro Asp Gly Asp Cys Arg Ser Asp Cys Gly Ser Ser Ala Ser
145                 150                 155                 160

Val Val Asp Asp Asp Cys Thr Asp Ala Ala Ala Ser Ala Ser Cys Pro
                165                 170                 175
```

-continued

```
Phe Pro Leu Pro Phe Asp Leu Asn Leu Pro Pro Gly Gly Gly Ala
            180                 185                 190

Gly Val Gly Phe Tyr Ala Asp Glu Glu Asp Glu Leu Arg Leu Thr Ala
            195                 200                 205

Leu Arg Leu
    210

<210> SEQ ID NO 46
<211> LENGTH: 194
<212> TYPE: PRT
<213> ORGANISM: Triticum aestivum
<220> FEATURE:
<221> NAME/KEY: misc_feature
<222> LOCATION: (1)..(194)
<223> OTHER INFORMATION: Ceres CLONE ID no. 1055099

<400> SEQUENCE: 46

Met Arg Lys Ala Arg Pro Pro Gln Pro Gln Pro Gln Pro Ser Gln Gln
1               5                   10                  15

Ser Pro Glu Ile Arg Tyr Arg Gly Val Arg Lys Arg Pro Ser Gly Arg
                20                  25                  30

Tyr Ala Ala Glu Ile Arg Asp Pro Ala Lys Lys Thr Pro Ile Trp Leu
            35                  40                  45

Gly Thr Phe Asp Cys Ala Glu Asp Ala Ala Arg Ala Tyr Asp Ser Ala
        50                  55                  60

Ala Arg Ser Leu Arg Gly Pro Thr Ala Arg Thr Asn Phe Pro Pro Ser
65                  70                  75                  80

Ser Ala Thr Gln Pro Pro Arg Pro Pro Pro Ala Ala Ala Ala
                85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Ala Arg Ser Ala Ala Arg Ala Gly
        115                 120                 125

Thr Ala Lys Glu Gly Glu Glu Asp Cys Arg Ser Tyr Cys Gly Ser Ser
    130                 135                 140

Ser Ser Val Leu Leu Glu Glu Gly Ala Asp Asp Ala Ala Ala Ser Arg
145                 150                 155                 160

Ser Pro Leu Pro Phe Asp Leu Asn Met Pro Pro Pro Gln Glu Gly Ala
                165                 170                 175

Leu Asp Ala Glu Ala Asp Gln Met Thr Cys Arg Tyr Asp Thr Leu Leu
            180                 185                 190

Arg Leu
```